US012731252B2

(12) United States Patent
Chen

(10) Patent No.: US 12,731,252 B2
(45) Date of Patent: Sep. 8, 2026

(54) SYSTEMS AND METHODS FOR IMAGE GUIDED TISSUE ABLATION

(71) Applicant: Gynesonics Inc., Redwood City, CA (US)

(72) Inventor: Jiayu Chen, Palo Alto, CA (US)

(73) Assignee: Gynesonics Inc., Redwood City, CA (US)

( * ) Notice: Subject to any disclaimer, the term of this patent is extended or adjusted under 35 U.S.C. 154(b) by 545 days.

(21) Appl. No.: 18/306,954

(22) Filed: Apr. 25, 2023

(65) Prior Publication Data

US 2023/0260121 A1 Aug. 17, 2023

Related U.S. Application Data

(63) Continuation of application No. PCT/US2021/056692, filed on Oct. 26, 2021.

(Continued)

(51) Int. Cl.
*G06T 7/00* (2017.01)
*A61B 18/00* (2006.01)

(Continued)

(52) U.S. Cl.
CPC ............ *G06T 7/0012* (2013.01); *G06V 10/44* (2022.01); *G06V 10/764* (2022.01); *G16H 20/00* (2018.01);

(Continued)

(58) Field of Classification Search
CPC combination set(s) only.
See application file for complete search history.

(56) References Cited

U.S. PATENT DOCUMENTS 6,540,677 B1 4/2003 Angelsen et al.
6,623,481 B1 9/2003 Garbagnati et al.

(Continued)

FOREIGN PATENT DOCUMENTS

WO WO-2019159090 A1 * 8/2019 ............. G16H 50/20
WO WO-2019246580 A1 12/2019
WO WO-2022093848 A1 5/2022

OTHER PUBLICATIONS

EP Serial No. 21887360.2 European Extended Search Report dated Sep. 25, 2024.

(Continued)

*Primary Examiner* — Vu Le
*Assistant Examiner* — Matthew James Bodnark
(74) *Attorney, Agent, or Firm* — Vista IP Law Group, LLP

(57) ABSTRACT

A real-time, intra-uterine operating field image is displayed to an operator. A processor identifies anatomical features and marks anatomical boundaries on the image with the aid of a trained classifier model. Labels for the identified anatomical features and the anatomical boundaries are displayed on the image. The trained classifier model is trained based on a set of prior surgical field images that have anatomical features and anatomical boundaries therein identified and marked, respectively, by previous operators. The trained classifier model is typically a convolutional deep neural network. The operator is allowed to modify the anatomical feature labels and anatomical boundaries, as well as update the set of training images with the modified image. The labeling of the anatomical features and establishment of the anatomical features facilitate performing treatments in the uterus, such as the ablation of uterine fibroids.

22 Claims, 19 Drawing Sheets

Related U.S. Application Data

(60) Provisional application No. 63/106,280, filed on Oct. 27, 2020.

(51) Int. Cl.
*G06V 10/44* (2022.01)
*G06V 10/764* (2022.01)
*G16H 20/00* (2018.01)
*G16H 30/40* (2018.01)

(52) U.S. Cl.
CPC .... *G16H 30/40* (2018.01); *A61B 2018/00559* (2013.01); *A61B 2018/00577* (2013.01); *G06T 2207/10132* (2013.01); *G06T 2207/30096* (2013.01)

(56) References Cited

U.S. PATENT DOCUMENTS 6,936,048 B2 8/2005 Hurst
6,944,490 B1 9/2005 Chow
6,969,354 B1 11/2005 Marian
7,160,296 B2 1/2007 Pearson et al.
7,229,401 B2 6/2007 Kindlein
7,387,628 B1 6/2008 Behl et al.
7,517,346 B2 4/2009 Sloan et al.
7,963,941 B2 6/2011 Wilk
8,080,009 B2 12/2011 Lee et al.
8,088,072 B2 1/2012 Munrow et al.
8,157,741 B2 4/2012 Hirota
8,157,745 B2 4/2012 Schoot
8,206,300 B2 6/2012 Deckman et al.
8,216,231 B2 7/2012 Behl et al.
8,221,321 B2 7/2012 Mcmorrow et al.
8,262,574 B2 9/2012 Placek et al.
8,262,577 B2 9/2012 Munrow et al.
8,287,485 B2 10/2012 Kimura et al.
8,377,041 B2 2/2013 Frassica et al.
8,469,893 B2 6/2013 Chiang et al.
8,512,330 B2 8/2013 Epstein et al.
8,512,333 B2 8/2013 Epstein et al.
8,540,634 B2 9/2013 Bruce et al.
8,585,598 B2 11/2013 Razzaque et al.
8,622,911 B2 1/2014 Hossack et al.
8,663,130 B2 3/2014 Neubach et al.
8,718,339 B2 5/2014 Tonomura et al.
8,814,796 B2 8/2014 Martin et al.
8,992,427 B2 3/2015 Munrow et al.
9,089,287 B2 7/2015 Sliwa et al.
9,198,707 B2 12/2015 Mckay et al.
9,198,719 B2 12/2015 Murdeshwar et al.
9,247,925 B2 2/2016 Havel et al.
9,439,627 B2 9/2016 Case et al.
9,510,898 B2 12/2016 Epstein et al.
9,516,996 B2 12/2016 Diolaiti et al.
9,861,336 B2 1/2018 Munrow et al.
10,321,951 B2 6/2019 Placek et al.
10,426,442 B1 10/2019 Schnorr
10,595,819 B2 3/2020 Deckman et al.
10,610,197 B2 4/2020 Deckman et al.
10,856,838 B2 12/2020 Munrow et al.
11,096,760 B2 8/2021 Munrow et al.
11,096,761 B2 8/2021 Munrow et al.
11,219,483 B2 1/2022 Chen et al.
11,564,735 B2 1/2023 Placek et al.
11,612,431 B2 3/2023 Chen
2008/0228081 A1 9/2008 Becker et al.
2009/0043295 A1 2/2009 Arnal et al.
2010/0056926 A1 3/2010 Deckman et al.
2010/0262133 A1 10/2010 Hoey et al.
2012/0035464 A1 2/2012 Raju et al.
2012/0165813 A1 6/2012 Lee et al.
2012/0209115 A1 8/2012 Tonomura
2012/0277737 A1 11/2012 Curley
2012/0316440 A1 12/2012 Munrow et al.
2013/0281863 A1 10/2013 Chiang et al.
2013/0317366 A1 11/2013 Hirayama et al.
2014/0180273 A1 6/2014 Nair
2014/0276081 A1 9/2014 Tegels
2015/0150497 A1 6/2015 Goldchmit
2015/0173592 A1 6/2015 Leeflang et al.
2015/0257779 A1 9/2015 Sinelnikov et al.
2016/0151041 A1 6/2016 Lee et al.
2016/0278740 A1 9/2016 Negrila et al.
2016/0310042 A1 10/2016 Kesten et al.
2017/0245838 A1 8/2017 Munrow et al.
2017/0245891 A1 8/2017 Munrow et al.
2019/0148011 A1 5/2019 Rao et al.
2019/0262080 A1 8/2019 Hammudi et al.
2019/0336101 A1* 11/2019 Chiang .................... A61B 1/00
2019/0350648 A1 11/2019 Owens et al.
2020/0229892 A1 7/2020 Munrow et al.
2021/0015450 A1 1/2021 Deckman et al.

OTHER PUBLICATIONS

PCT/US2021/056692 International Search Report and Written Opinion dated Feb. 24, 2022.

* cited by examiner

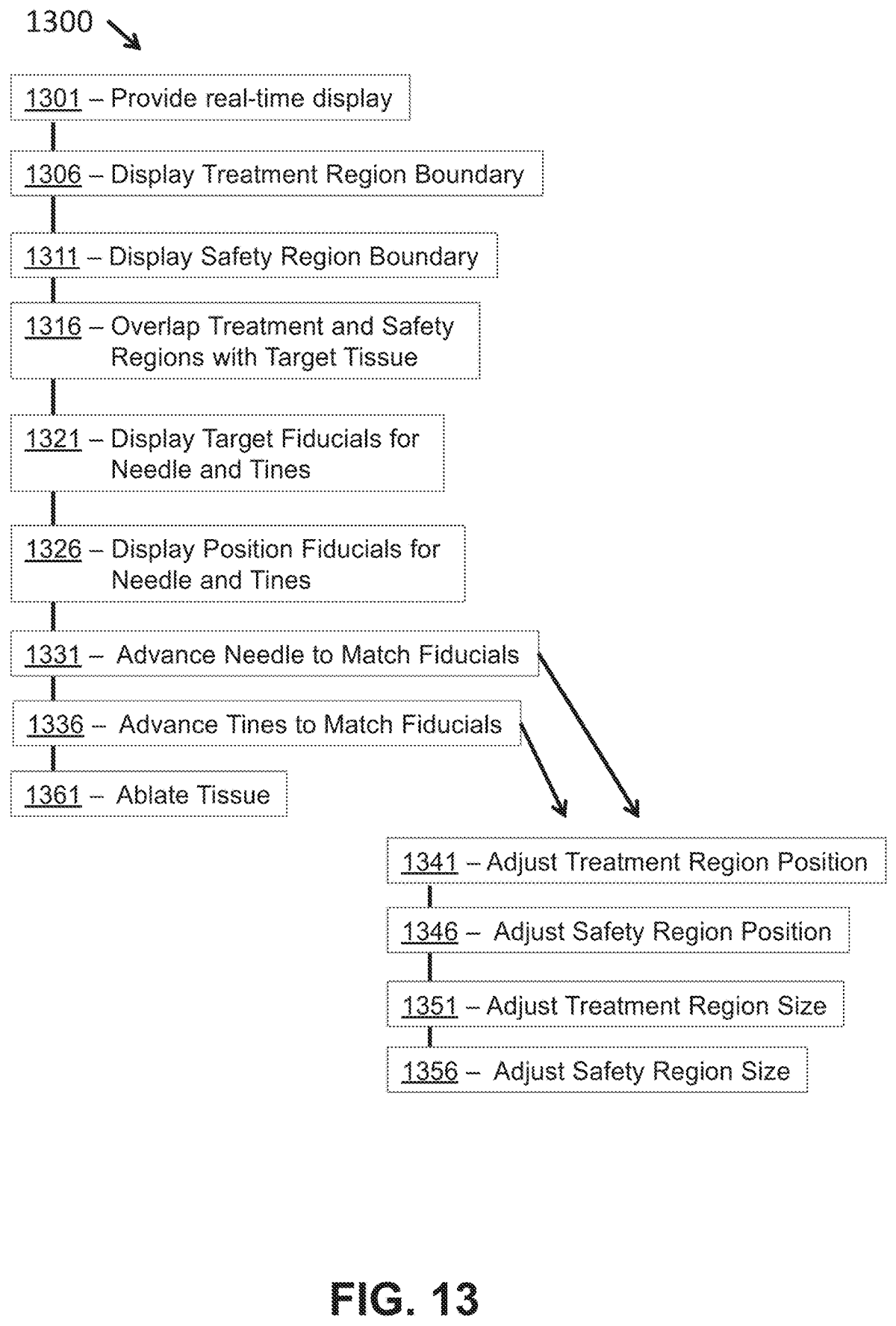

1300

1301 – Provide real-time display

1306 – Display Treatment Region Boundary

1311 – Display Safety Region Boundary

1316 – Overlap Treatment and Safety Regions with Target Tissue

1321 – Display Target Fiducials for Needle and Tines

1326 – Display Position Fiducials for Needle and Tines

1331 – Advance Needle to Match Fiducials

1336 – Advance Tines to Match Fiducials

1361 – Ablate Tissue

1341 – Adjust Treatment Region Position

1346 – Adjust Safety Region Position

1351 – Adjust Treatment Region Size

1356 – Adjust Safety Region Size

FIG. 13

SYSTEMS AND METHODS FOR IMAGE GUIDED TISSUE ABLATION

CROSS-REFERENCE

This application is a continuation of PCT Application No. PCT/US21/56692, filed Oct. 26, 2021; which claims the benefit of U.S. Provisional Application No. 63/106,280, filed Oct. 27, 2020; the contents of which are incorporated in their entirety herein by reference.

The subject matter of this application is related to that of U.S. patent application Ser. No. 12/245,567, filed on Oct. 3, 2008 and now issued as U.S. Pat. No. 8,088,072 on Jan. 3, 2012, Ser. No. 13/307,304, filed on Nov. 30, 2011 and now issued as U.S. Pat. No. 8,262,577 on Sep. 11, 2012, Ser. No. 13/589,975, filed on Aug. 20, 2012, Ser. No. 15/595,659, filed May 15, 2017, Ser. No. 15/597,511, filed May 17, 2017, Ser. No. 16/841,201, filed Apr. 8, 2020, Ser. No. 17/028,593, filed Sep. 22, 2020, Ser. No. 17/028,596, filed Sep. 22, 2020, Ser. No. 12/198,861, filed on Aug. 26, 2008, Ser. No. 13/023,383, filed on Feb. 8, 2011 and now issued as U.S. Pat. No. 8,206,300, Ser. No. 14/989,732, filed on Jan. 6, 2016 and now issued as U.S. Pat. No. 10,610,197 on Apr. 7, 2020, Ser. No. 13/484,076, filed on May 30, 2012 and now issued as U.S. Pat. No. 10,595,819 on Mar. 24, 2020, Ser. No. 16/782,477, filed on Feb. 5, 2020, Ser. No. 12/712,969, filed on Feb. 25, 2010 and now issued as U.S. Pat. No. 8,262,574 on Sep. 11, 2012, Ser. No. 13/589,956, filed Aug. 20, 2012 and now issued as U.S. Pat. No. 10,321,951, Ser. No. 16/417,193, filed May 20, 2019, Ser. No. 15/793,874, filed Oct. 25, 2017, Ser. No. 13/801,782, filed Mar. 13, 2013 and now issued as U.S. Pat. No. 9,861,336, Ser. No. 13/801,840, filed Mar. 13, 2013 and now issued as U.S. Pat. No. 8,992,427, Ser. No. 15/811,520, filed Nov. 13, 2017, Ser. No. 16/408,790, filed May 10, 2019, and Ser. No. 16/666,271, filed Oct. 28, 2019, Ser. No. 16/414,040, filed May 16, 2019, the contents of which are fully incorporated by reference herein.

BACKGROUND

The present disclosure relates generally to systems and methods for guiding an operator before and during surgery, such as by guiding the operator or surgeon using surgical field images that have been marked, labeled, and/or provided with anatomical boundaries. The systems and methods provided herein may find particular use in medical methods and apparatus involving tissue ablation.

Current medical treatments of organs and tissues within a patient's body often use a needle or other elongate body for delivery of energy, therapeutic agents, or the like. Optionally, the methods use ultrasound or other imaging to observe and identify a treatment target and track the position of the needle relative to the treatment target. In many cases, the operator must manually identify treatment target and mark its boundaries. Many surgical systems, such as the Sonata® System available from Gynesonics, Inc. of Redwood City, CA, allow the operator to label the identified treatment target and mark anatomical boundaries on the visual display of the system. The identification of treatment targets and/or anatomical features and the marking of anatomical boundaries may vary from operator to operator, the identification of treatment targets and marking of anatomical boundaries can consume valuable surgical time, and the treatment target and surrounding anatomy may move and deviate from the original marked boundaries over the course of a surgical procedure. Accordingly, systems and methods for improved image guided tissue ablation in which anatomical features and boundaries are identified and marked more consistently and quickly may be desired.

Of particular interest to the present disclosure, a treatment for uterine fibroids has recently been proposed which relies on the transvaginal or laparoscopic positioning of a treatment probe or device in the patient's uterus. A radiofrequency or other energy or therapeutic delivery needle is deployed from the device into the fibroid, and energy and/or therapeutic substances are delivered in order to ablate or treat the fibroid. To facilitate locating the fibroids and positioning the needles within the fibroids, the treatment device includes an ultrasonic or other imaging array with an adjustable field of view in a generally forward or lateral direction relative to an axial shaft which carries the needle. The needle is advanced from the shaft and across the field of view so that the needle can be visualized and directed into the tissue and the targeted fibroid. The intra-uterine image captured by the ultrasonic imaging array is viewed by the operator or surgeon to guide the positioning and advancement of the needle, and the system may allow the operator to label the identified treatment target and mark anatomical boundaries on the visual display of the system.

It would further be desirable to provide improved systems and methods for the guided deployment of energy delivery and other needles within ultrasonic or other imaging fields of view in energy delivery or other therapeutic protocols. It would be particularly useful to provide the operator or treating physician with information which would assist in initial positioning and deployment of a plurality of needles or tines in order to improve the likelihood that the needle assembly will be properly positioned relative to a targeted anatomy to be treated. It would also be desirable to provide feedback to the operator to assist in adjusting a treatment procedure based on information that has been updated during the procedure. Such information should allow the operator, if necessary, to reposition the probe in order to increase the likelihood of fully treating the anatomy. All such feedback or other information is preferably provided visually on the ultrasonic or other imaging screen so that the needle position can be quickly predicted, assessed, and treatment initiated. It would be further desirable if the information were presented on a display screen in response to manipulating the probe and/or changing the anatomy while minimizing the need to enter data or commands onto a system controller or display. At least some of these objectives will be met by the many embodiments described hereinafter.

SUMMARY

The present disclosure provides systems and methods for guiding an operator before and during treatment procedures such as surgery, such as by guiding the operator or surgeon using real-time operating field images that have been marked, labeled, and/or provided with anatomical boundaries. The marking, labeling, and/or anatomical boundaries may be suggested automatically by a treatment system as provided by a classifier model. By providing suggested labels and boundaries for anatomical structures and features, the treatment procedure workflow may be streamlined. The classifier model may be trained based on prior surgical field images that have been marked, labeled, and/or provided with anatomical boundaries by prior operators. The suggested marks, labels, and/or anatomical boundaries may be updated by the operator and the training set and the classifier model may be updated accordingly, such that the classifier model can be improved over multiple iterations. The suggested marks, labels, and/or anatomical boundaries may be updated, for example, in real-time, while the treatment procedure is implemented to account for any changes in anatomy as a result of the treatment procedure.

The systems and methods provided herein may find particular use in methods and systems for treating uterine fibroids, such as those involving the deployment of diagnostic and therapeutic structures, such as needles and/or tines, in tissue such as uterine fibroids. Needle structures may in some cases comprise a single needle but, in most cases, will comprise multiple needles or needle and tine assemblies as described in more detail below. The needle structures are usually intended to deliver a therapy to the tissue, most typically being configured to deliver radiofrequency energy, plasma energy, therapeutic ultrasound energy, microwave energy, heat, cold (cryogenic treatment), or other energy to ablate or otherwise modify a target tissue or targeted anatomy within the tissue. Alternatively or in combination, the needle structures could also provide drug or other substance delivery, morcellation, or other tissue treatments which can be effected using a needle structure, or may be diagnostic needle structures for diagnostic procedures such as imaging, tissue mapping, and biopsy.

The methods and systems of the present disclosure may be particularly suitable for treating fibroids in a patient's uterus where a treatment probe carrying the needle structure and an imaging transducer, typically an ultrasonic imaging transducer, is introduced transvaginally and transcervically into the uterus, or in other cases laparoscopically into and through an exterior of the uterus or other organ or tissue target. The treatment probe may be manipulated within the uterus to deliver ablative energy to the fibroid as described in more detail below. In most embodiments of the present disclosure, the needle structure is "virtually" deployed on a real-time image of the tissue prior to actual deployment of the needle in the actual tissue. In many embodiments, anatomical features can be labeled, and anatomical boundaries can be marked in the real-time image, and the needle structure may be "virtually" deployed to a labeled anatomical feature which is separated from the rest of the anatomy by the marked boundar(ies). The anatomical features can be labeled, and the anatomical boundaries can be marked by a combination of suggestions from the classifier model and manually by the operator. Treatment and/or safety boundaries within the tissue will also be determined and optionally adjusted prior to and/or during the actual deployment of the needle structure. In many embodiments, the actual position of the needle structure may be tracked, and the corresponding treatment and/or safety boundaries may be projected on the screen in real time. In many embodiments, both the deployment of the needle structure and adjustment of the displayed treatment and/or safety boundaries are controlled with a handle of the treatment probe. The treatment and safety boundaries can be checked before treatment is commenced.

The methods and systems of the present disclosure may further provide that, once the parameters of the virtual deployment have been selected using the virtual images, the needle structure can actually be deployed in the real tissue at a location and/or in a pattern which matches the virtual deployment configuration. This system may track the position of the treatment probe and/or needle structure in the uterus, thus allowing treatment and safety boundaries which may be projected upon the real-time image of the tissue to be calculated and/or updated as the treatment probe is moved and the needle structure advanced by the treating operator. One or more controls elements on the treatment probe handle may be manipulated to move, translate, enlarge, shrink, or otherwise adjust or re-position the treatment and safety boundaries displayed. In many embodiments, the one or more control elements may be manipulated to establish one or more "stop" positions corresponding to the user-desired limits to needle deployment and/or to a user-defined deployment pattern, which will typically be within the treatment and safety boundaries. The treatment and safety boundaries may be calculated by the system based on the user-defined "stop" positions as well as on energy delivery data which may be supplied to or generated by a system controller. Once the treatment region and/or safety boundary are properly established and positioned on the real-time image relative to the anatomy to be treated, the operator may hold the treatment probe in place and use the control handle to deploy the needle structure until it reaches its "stop" position(s) which have typically been preset into the treatment probe during the initial imaging and set-up phase of the treatment. In some cases, the stops can be automatically set as the operator manipulates the treatment and/or safety boundary on the screen using the controls on the treatment probe. In alternative embodiments, the operator may manipulate the treatment probe and advance the needle structure while viewing the safety and/or treatment boundaries in real time without having previewed the virtual projections.

In the exemplary embodiments, at least one main or central needle will be deployed from the treatment probe, and a plurality of tines or secondary needles will be deployed from the main or central needle(s). Most often, there will be a single main needle which is deployed distally from a shaft of the treatment probe along a central axis thereof. A plurality of tines may then be advanced from the single needle in a distally diverging pattern. In other embodiments, a plurality of needles or tines may be advanced from the treatment probe without use of a main or central needle. In such cases, the needles or tines will typically expand or diverge into a three-dimensional array as they are advanced distally.

Exemplary anatomical features that may be imaged and subsequently treated include fibroids, tumors, encapsulated tissue masses, pseudo-encapsulated tissue masses, and the like. Of particular interest of the present disclosure, the treatment probe may be positioned in the uterus and the needle structure deployed to a location proximate to or within a fibroid located in the myometrium tissue of the uterus. In such cases, it will be desirable to also image the serosa which surrounds the myometrium and/or other sensitive anatomical features that could be damaged by the energy-mediated treatments described herein.

As used herein, a treatment region is defined by a treatment boundary which is calculated by the system controller or established by the user based upon the needle structure deployment configuration (either as set by the virtual "stops" or as calculated in real-time as the needle structure is deployed) and the energy delivery parameters set by or input into the system controller. Energy or other therapy delivered by the needle structure deployed in the selected pattern at the selected location will effectively treat the target tissue to achieve ablation or other therapeutic results. As described below, it will thus be desirable to manipulate the treatment probe as well as the needle structure stop(s) and/or actual needle structure so that the treatment region at least partially surrounds the anatomy to be treated as seen on the real-time image display of the system.

As further used herein, the safety region is defined by a safety boundary which is calculated by the system or established by the user. As with the treatment region, the safety boundary is calculated or established by the user based upon the virtual "stops" of the needle structure, actual needle structure positions which have been set or adjusted on the treatment probe by the operator, and/or the energy delivery parameters which are input into or set by the system controller. The safety boundary will differ from the treatment boundary in that the safety boundary will be set at a minimum threshold distance beyond the boundary of the tissue treatment region where the risk of damaging tissue is reduced or eliminated entirely.

In an aspect of the present disclosure, the safety boundary is used dynamically with the movement of anatomic structure during the procedure. The treatment device configuration will be changed manually or automatically based on the changes.

Aspects of the present disclosure provide computer-implemented methods of planning and implementing treatment procedures. An exemplary procedure may comprise the steps of: (i) displaying a real-time operating field image to an operator; (ii) identifying one or more of (a) at least one anatomical feature or (b) at least one anatomical boundary on the real-time operating field image, with the aid of the trained classifier model; (iii) displaying one or more of (a) at least one label for the identified at least one anatomical feature or (b) at least one marking for the identified at least one anatomical boundary on the displayed real-time operating field image; (iv) allowing the operator to modify the real-time operating field image by one or more of (a) re-labelling the identified at least one anatomical feature or (b) re-positioning the at least one marking for the at least one anatomical boundary; and (v) provide an update to the trained classifier model based on the modifications by the operator.

In some embodiments, the trained classifier model is generated by the steps of: (vi) displaying an operating field image to a user; (vii) establishing at least one anatomical boundary in the operating field image, the at least one anatomical boundary being marked by the user; (viii) labelling at least one anatomical feature separated by the at least one anatomical boundary in the operating field image, the at least one anatomical feature being labeled by user; and (ix) repeating steps (vi) to (viii) to generate a training set of operating field images each with at least one marked anatomical boundary and at least one labeled anatomical feature; and (x) training a classifier model, based on the training set of operating field images, to identify (a) at least one anatomical feature or (b) at least one anatomical boundary on the real-time operating image. The trained classifier model may be updated at step (v) by adding the modified real-time operating field image from step (iv) to the training set of operating field images and updating the classifier model based on the set of operating field images with the added modified real-time operating field image.

In some embodiments, the method further comprises a step of comprising confirming with the operator the one or more of (a) the re-labelled identified at least one anatomical feature or (b) the re-positioned at least one marking for the at least one anatomical boundary before providing the update to the trained classifier model. The step of providing the update to the trained classifier model may comprise a step of adding the modified real-time operating field image to a training set of operating field images.

In some embodiments, the operating field image at step (i) is a surgical field image.

In some embodiments, the method further comprises a step of treating an anatomical structure based on one or more of (a) the displayed at least one label for the at least one identified anatomical feature or (b) the displayed at least one marking for the at least one anatomical boundary on the real-time operating field image. The step of treating the anatomical structure may comprise ablating the anatomical structure. The anatomical structure may be ablated using one or more of radiofrequency (RF) energy, plasma energy, therapeutic ultrasound energy, microwave energy, heat, or cold. The treated anatomical structure may be a uterine fibroid. The method may further comprise repeating steps (ii) to (iv) in real-time during the treatment procedure. The method may further comprise repeating one or more of steps (ii) or (iii) after the treatment procedure to identify one or more changes to the anatomical structure from the treatment procedure, for example, to identify the tissue changes as a part of after treatment documentation.

In some embodiments, the operating field image at step (i) comprises an ultrasound image. The ultrasound image may be an intra-uterine ultrasound image.

In some embodiments, the operating field image at step (i) comprises an image of a uterus of a patient. The at least one marking for the at least one anatomical boundary may separate a plurality of anatomical features of the uterus. The plurality of anatomical features may include one or more of a serosa, a myometrium, a fibroid, a uterine wall, a bladder wall, or a bladder. The at least one label for the at least one anatomical feature may include one or more of a serosa, a myometrium, a fibroid, a uterine wall, a bladder wall, or a bladder.

In some embodiments, the trained classifier model may comprise a machine learning algorithm. The machine learning algorithm may be a convolutional deep learning network, for example.

In some embodiments, the trained classifier model is one or more of a binary tree, a random forest, a decision tree, a plurality of decision trees, a plurality of decision trees with controlled variance, a multinomial logistic regression, a naïve Bayes classifier, a linear classifier, an ensemble of linear classifiers, a boosting algorithm, a boosting algorithm trained with stochastic gradient descent, a boosting algorithm trained with stochastic gradient descent, a boosting algorithm comprising training data weighting, a boosting algorithm comprising updating training data weighting, or a boosting algorithm comprising updating misclassified training data with higher weights.

In some embodiments, the method further comprises providing a pre-treatment image to the operator as a guide for identifying the one or more of (a) the at least one anatomical feature or (b) the at least one anatomical boundary on the real-time operating field image. The pre-treatment image may be pre-labelled with suggested or recommended identifiers for one or more anatomical structures, which has been pre-labelled by a classifier model, may rely on input from an operator or user to label or identify one or more anatomical structures, or a combination of both. The pre-treatment image may comprise one or more of an MRI image, an X-ray image, a CT image, or an ultrasound image.

Aspects of the present disclosure provide apparatuses for aiding in planning and implementing a treatment procedure. An exemplary apparatus may comprise a display; an interface; a processor; and a non-transitory computer readable storage medium including instructions configured to cause the processor to: (i) cause the display to display a real-time operating field image to an operator, (ii) identify one or more of (a) at least one anatomical feature or (b) at least one anatomical boundary on the real-time operating field image, with the aid of the trained classifier model, (iii) display one or more of (a) at least one label for the identified at least one anatomical feature or (b) at least one marking for the identified at least one anatomical boundary on the displayed real-time operating field image, (iv) allow the operator to modify the real-time operating field image by one or more of (a) re-labelling the at least one identified anatomical features or (b) re-positioning the at least one marking for the at least one identified anatomical boundary, and (v) provide an update to the trained classifier model based on the modifications by the operator.

In some embodiments, the instructions are further configured to cause the processor to: (vi) display an operating field image to a user; (vii) establish at least one anatomical boundary in the operating field image, the at least one anatomical boundary being marked by the user via the interface; (viii) label at least one anatomical feature separated by the at least one anatomical boundary, the at least one anatomical feature being labeled by the user via the interface; (ix) repeat steps (vi) to (viii) to generate a training set of operating field images each with at least one marked anatomical boundary and at least one labeled anatomical feature; and (x) train a classifier model, based on the training set of operating field images, to at least one of (a) identify at least one anatomical feature or (b) establish at least one anatomical boundary on the real-time operating image. The trained classifier model may be updated at step (v) by adding the modified real-time operating field image from step (iv) to the training set of operating field images and updating the classifier model based on the set of operating field images with the added modified real-time operating field image.

In some embodiments, the instructions are further configured to cause the processor to confirm with the operator the one or more of (a) the re-labelled at least one anatomical feature or (b) the re-positioned at least one marking for the at least one anatomical boundary before providing the update to the trained classifier model. The update may be provided to the trained classifier model by adding the modified real-time operating field image to a training set of operating field images.

In some embodiments, the operating field image at step (i) is an operating field image.

In some embodiments, the instructions are further configured to cause the processor to further allow the operator to use the interface to treat an anatomical structure based on one or more of (a) the displayed at least one label for the at least one identified anatomical feature or (b) the displayed at least one marking for the at least one anatomical boundary on the real-time operating field image. The step of treating the anatomical structure may comprise ablating the anatomical structure with an ablation element, and the apparatus may further comprise the ablation element. The ablation element may be configured to delivery one or more of radiofrequency (RF) energy, plasma energy, therapeutic ultrasound energy, microwave energy, heat, or cold to the anatomical structure. The treated anatomical structure may be a uterine fibroid. The instructions may be further configured to cause the processor to repeat steps (ii) to (iv) in real-time during the treatment procedure. The instructions may be further configured to cause the processor to repeat one or more of steps (ii) or (iii) after the treatment procedure to identify one or more changes to the anatomical structure from the treatment procedure, for example, to identify the tissue changes as a part of after treatment documentation.

In some embodiments, the operating field image at step (i) comprises an ultrasound image. The ultrasound image may be an intra-uterine ultrasound image.

In some embodiments, the operating field image at step (i) comprises an image of a uterus of a patient. The at least one marking for the at least one anatomical boundary may separate a plurality of anatomical features of the uterus, the plurality of anatomical features including one or more of a serosa, a myometrium, a fibroid, a uterine wall, a bladder wall, or a bladder. The at least one label for the at least one anatomical feature may include one or more of a serosa, a myometrium, a fibroid, a uterine wall, a bladder wall, or a bladder.

In some embodiments, the classifier model comprises a machine learning algorithm. The machine learning algorithm may be a convolutional deep learning network, for example.

In some embodiments, the classifier model is one or more of a binary tree, a random forest, a decision tree, a plurality of decision trees, a plurality of decision trees with controlled variance, a multinomial logistic regression, a naïve Bayes classifier, a linear classifier, an ensemble of linear classifiers, a boosting algorithm, a boosting algorithm trained with stochastic gradient descent, a boosting algorithm trained with stochastic gradient descent, a boosting algorithm comprising training data weighting, a boosting algorithm comprising updating training data weighting, or a boosting algorithm comprising updating misclassified training data with higher weights.

In some embodiments, the instructions are further configured to cause the processor to further provide a pre-treatment image to the operator as a guide for identifying the one or more of (a) the at least one anatomical feature or (b) the at least one anatomical boundary on the real-time operating field image. The pre-treatment image may be pre-labelled with suggested or recommended identifiers for one or more anatomical structures, which has been pre-labelled by a classifier model, may rely on input from an operator or user to label or identify one or more anatomical structures, or a combination of both. The pre-treatment image comprises one or more of an MRI image, an X-ray image, a CT image, or an ultrasound image.

Aspects of the present disclosure provide computer-implemented methods of planning and implementing a treatment procedure. An exemplary computer-implemented method may comprise steps of: (i) displaying a real-time operating field image to an operator; (ii) identifying one or more of (a) at least one anatomical feature or (b) at least one anatomical boundary on the real-time operating field image, with the aid of a trained classifier model; and (iii) displaying one or more of (a) at least one label for the identified at least one anatomical feature or (b) at least one marking for the at least one anatomical boundary on the real-time operating field image. The trained classifier model may be trained based on a set of operating field images each with at least one marked anatomical boundary and at least one labeled anatomical feature. The at least one marked anatomical boundary may be identified by a previous operator. The at least one labeled anatomical feature may be identified by the previous operator.

In some embodiments, the method further comprises a step of allowing the operator to modify the real-time operating field image by one or more of (a) re-labelling the identified at least one anatomical feature or (b) re-positioning the identified at least one anatomical boundary. The method may further comprise a step of updating the set of operating field images by adding the modified real-time operating field image to the set. The method may further comprise a step of comprising updating the classifier model based on the updated set of operating field images.

In some embodiments, the method further comprises a step of treating an anatomical structure based on one or more of (a) the displayed at least one label for the identified at least one anatomical feature or (b) the displayed at least one marking for the at least one anatomical boundary on the real-time surgical field image. The method may further comprise a step of treating the anatomical structure comprises ablating the anatomical structure. The anatomical structure may be ablated using one or more of radiofrequency (RF) energy, plasma energy, therapeutic ultrasound energy, microwave energy, heat, or cold. The treated anatomical structure may be a uterine fibroid. The instructions may be further configured to cause the processor to repeat steps (ii) and (iii) in real-time during the treatment procedure. The instructions may be further configured to cause the processor to repeat one or more of steps (ii) or (iii) after the treatment procedure to identify one or more changes to the anatomical structure from the treatment procedure, for example, to identify the tissue changes as a part of after treatment documentation.

In some embodiments, the real-time operating field image comprises an ultrasound image. The ultrasound image may be an intra-uterine ultrasound image.

In some embodiments, the identified at least one anatomical boundary separates a plurality of anatomical features of a uterus, the plurality of anatomical features including one or more of a serosa, a myometrium, a fibroid, a uterine wall, a bladder wall, or a bladder.

In some embodiments, the at least one labeled anatomical feature includes one or more of a serosa, a myometrium, a fibroid, a uterine wall, a bladder wall, or a bladder.

In some embodiments, the classifier model comprises a machine learning algorithm. The machine learning algorithm may be a convolutional deep learning network, for example.

In some embodiments, the classifier model is one or more of a binary tree, a random forest, a decision tree, a plurality of decision trees, a plurality of decision trees with controlled variance, a multinomial logistic regression, a naïve Bayes classifier, a linear classifier, an ensemble of linear classifiers, a boosting algorithm, a boosting algorithm trained with stochastic gradient descent, a boosting algorithm trained with stochastic gradient descent, a boosting algorithm comprising training data weighting, a boosting algorithm comprising updating training data weighting, or a boosting algorithm comprising updating misclassified training data with higher weights.

In some embodiments, the method further comprises providing a pre-treatment image to the operator as a guide for identifying the one or more of (a) the at least one anatomical feature or (b) the at least one anatomical boundary on the real-time operating field image. The pre-treatment image may be pre-labelled with suggested or recommended identifiers for one or more anatomical structures, which has been pre-labelled by a classifier model, may rely on input from an operator or user to label or identify one or more anatomical structures, or a combination of both. The pre-treatment image may comprise one or more of an MRI image, an X-ray image, a CT image, or an ultrasound image.

Aspects of the present disclosure provide apparatus for aiding in performing implementing a treatment procedure. An exemplary apparatus may comprise: a display; an interface; a processor; and a non-transitory computer readable storage medium including instructions configured to cause the processor to: (i) display a real-time operating field image to an operator; (ii) identify one or more of (a) at least one anatomical feature or (b) at least one anatomical boundary on the real-time operating field image, with the aid of a trained classifier model; and (iii) display one or more of (a) at least one label for the identified at least one anatomical feature or (b) at least one marking for the identified at least one anatomical boundary on the real-time operating field image. The trained classifier model may be trained based on a set of operating field images each with at least one marked anatomical boundary and at least one labeled anatomical feature. The at least one marked anatomical boundary may be identified by a previous operator. The at least one labeled anatomical feature may be identified by the previous operator.

In some embodiments, the instructions are further configured to cause the processor to allow the operator to modify the real-time operating field image by one or more of (a) re-labelling the identified at least one anatomical feature or (b) re-positioning the identified at least one anatomical boundary. The instructions may be further configured to cause the processor to update the set of operating field images by adding the modified real-time operating field image to the set. The instructions may be further configured to cause the processor to further update the classifier model based on the updated set of operating field images.

In some embodiments, the instructions are further configured to cause the processor to further allow the operator to use the interface to treat an anatomical structure based on one or more of (a) the displayed at least one label for the identified at least one anatomical feature or (b) the displayed at least one marking for the at least one anatomical boundary on the real-time surgical field image. Treating the anatomical structure may comprise ablating the anatomical structure with an ablation element. The apparatus may further comprise the ablation element. The ablation element may be configured to delivery one or more of radiofrequency (RF) energy, plasma energy, therapeutic ultrasound energy, microwave energy, heat, or cold to the anatomical structure. The treated anatomical structure may be a uterine fibroid. The instructions may be further configured to cause the processor to repeat one or more of steps (ii) or (iii) after the treatment procedure to identify one or more changes to the anatomical structure from the treatment procedure, for example, to identify the tissue changes as a part of after treatment documentation.

In some embodiments, the real-time operating field image comprises an ultrasound image. The ultrasound image may be an intra-uterine ultrasound image.

In some embodiments, the real-time operating field image comprises an image of a uterus of a patient.

In some embodiments, the identified at least one anatomical boundary separates a plurality of anatomical features of the uterus. The plurality of anatomical features may include one or more of a serosa, a myometrium, a fibroid, a uterine wall, a bladder wall, or a bladder.

In some embodiments, the at least one labeled anatomical feature includes one or more of a serosa, a myometrium, a fibroid, a uterine wall, a bladder wall, or a bladder.

In some embodiments, the classifier model comprises a machine learning algorithm. The machine learning algorithm may be a convolutional deep learning network. The classifier model may be one or more of a binary tree, a random forest, a decision tree, a plurality of decision trees, a plurality of decision trees with controlled variance, a multinomial logistic regression, a naïve Bayes classifier, a linear classifier, an ensemble of linear classifiers, a boosting algorithm, a boosting algorithm trained with stochastic gradient descent, a boosting algorithm trained with stochastic gradient descent, a boosting algorithm comprising training data weighting, a boosting algorithm comprising updating training data weighting, or a boosting algorithm comprising updating misclassified training data with higher weights.

In some embodiments, the instructions are further configured to cause the processor to further provide a pre-treatment image to the operator as a guide for identifying the one or more of (a) the at least one anatomical feature or (b) the at least one anatomical boundary on the real-time operating field image. The pre-treatment image may be pre-labelled with suggested or recommended identifiers for one or more anatomical structures, which has been pre-labelled by a classifier model, may rely on input from an operator or user to label or identify one or more anatomical structures, or a combination of both. The pre-treatment image comprises one or more of an MRI image, an X-ray image, a CT image, or an ultrasound image.

Aspects of the present disclosure provide computer-implemented methods of planning and implementing a treatment procedure. An exemplary method may comprise steps of: (i) displaying a real-time operating field image to an operator; (ii) identifying one or more of (a) at least one anatomical feature or (b) at least one anatomical boundary on the real-time operating field image, with the aid of the trained classifier model; (iii) displaying one or more of (a) at least one label for the identified at least one anatomical feature or (b) at least one marking for the identified at least one anatomical boundary on the displayed real-time operating field image; and (iv) treating an anatomical structure based on one or more of (a) the displayed at least one label for the identified at least one anatomical feature or (b) the displayed at least one marking for the identified at least one anatomical boundary on the real-time operating field image.

In some embodiments, the real-time operating field image is a real-time surgical field image.

In some embodiments, the real-time operating field image is an ultrasound image. The ultrasound image may be an intra-uterine ultrasound image.

In some embodiments, the operating field image is an image of a uterus of a patient. The identified at least one anatomical boundary may separate a plurality of anatomical features of the uterus, the plurality of anatomical features including one or more of a serosa, a myometrium, a fibroid, a uterine wall, a bladder wall, or a bladder. The identified at least one anatomical feature may include one or more of a serosa, a myometrium, a fibroid, a uterine wall, a bladder wall, or a bladder.

In some embodiments, the step of treating the anatomical structure comprises ablating the anatomical structure. The anatomical structure may be ablated using one or more of radiofrequency (RF) energy, plasma energy, therapeutic ultrasound energy, microwave energy, heat, or cold.

In some embodiments, the treated anatomical structure is a uterine fibroid.

In some embodiments, the trained classifier model comprises a machine learning algorithm.

In some embodiments, the method further comprises the steps of: allowing the operator to modify the real-time operating field image by one or more of (a) re-labelling the identified at least one anatomical feature or (b) re-positioning the marked at least one anatomical boundary; and providing an update to the trained classifier model based on the modifications by the operator.

In some embodiments, the method further comprises repeating steps (ii) and (iii) during the treatment procedure.

In some embodiments, the method further comprises repeating one or more of steps (ii) or (iii) after the treatment procedure to identify one or more changes to the anatomical structure from the treatment procedure, for example, to identify the tissue changes as a part of after treatment documentation.

In some embodiments, the method further comprises providing a pre-treatment image to the operator as a guide for identifying the one or more of (a) the at least one anatomical feature or (b) the at least one anatomical boundary on the real-time operating field image. The pre-treatment image may be pre-labelled with suggested or recommended identifiers for one or more anatomical structures, which has been pre-labelled by a classifier model, may rely on input from an operator or user to label or identify one or more anatomical structures, or a combination of both. The pre-treatment image may comprise one or more of an MRI image, an X-ray image, a CT image, or an ultrasound image.

Aspects of the present disclosure provide apparatuses for aiding in implementing a treatment procedure. An exemplary apparatus may comprise: a display; an interface; a processor; and a non-transitory computer readable storage medium including instructions configured to cause the processor to: (i) display a real-time operating field image to an operator; (ii) identify one or more of (a) at least one anatomical feature or (b) at least one anatomical boundary on the real-time operating field image, with the aid of the trained classifier model; (iii) display one or more of (a) at least one label for the identified at least one anatomical feature or (b) at least one marking for the identified at least one anatomical boundary on the displayed real-time operating field image; and (iv) treat an anatomical structure based on one or more of (a) the displayed at least one label for the identified at least one anatomical feature or (b) the displayed at least one marking for the identified at least one anatomical boundary on the real-time operating field image.

In some embodiments, the real-time operating field image is a real-time surgical field image.

In some embodiments, the real-time operating field image is an ultrasound image. The ultrasound image may be an intra-uterine ultrasound image.

In some embodiments, the operating field image is an image of a uterus of a patient. The identified at least one anatomical boundary may separate a plurality of anatomical features of the uterus, the plurality of anatomical features including one or more of a serosa, a myometrium, a fibroid, a uterine wall, a bladder wall, or a bladder. The identified at least one anatomical feature may include one or more of a serosa, a myometrium, a fibroid, a uterine wall, a bladder wall, or a bladder.

In some embodiments, the step of treating the anatomical structure comprises ablating the anatomical structure, and the apparatus further comprises an ablation element. The ablation element may be configured to ablate the anatomical structure using one or more of radiofrequency (RF) energy, plasma energy, therapeutic ultrasound energy, microwave energy, heat, or cold.

In some embodiments, the treated anatomical structure is a uterine fibroid.

In some embodiments, the trained classifier model comprises a machine learning algorithm.

In some embodiments, the instructions are further configured to cause the processor to: allow the operator to modify the real-time operating field image by one or more of (a) re-labelling the identified at least one anatomical feature or (b) re-positioning the marked at least one anatomical boundary; and provide an update to the trained classifier model based on the modifications by the operator.

In some embodiments, the instructions are further configured to cause the processor to repeat steps (ii) and (iii) during the treatment procedure.

In some embodiments, the instructions are further configured to cause the processor to repeat one or more of steps (ii) or (iii) after the treatment procedure to identify one or more changes to the anatomical structure from the treatment procedure, for example, to identify the tissue changes as a part of after treatment documentation.

In some embodiments, the instructions are further configured to cause the processor to further provide a pre-treatment image to the operator as a guide for identifying the one or more of (a) the at least one anatomical feature or (b) the at least one anatomical boundary on the real-time operating field image. The pre-treatment image may be pre-labelled with suggested or recommended identifiers for one or more anatomical structures, which has been pre-labelled by a classifier model, may rely on input from an operator or user to label or identify one or more anatomical structures, or a combination of both. The pre-treatment image may comprise one or more of an NMI image, an X-ray image, a CT image, or an ultrasound image.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the present disclosure are set forth with particularity in the appended claims. A better understanding of the features and advantages of the present disclosure will be obtained by reference to the following detailed description that sets forth illustrative embodiments, in which the principles of the present disclosure are utilized, and the accompanying drawings of which:

FIG. 13 illustrates a flow chart of a method of treating tissue, in accordance with the principles of the present disclosure.

DETAILED DESCRIPTION

Figure 1:
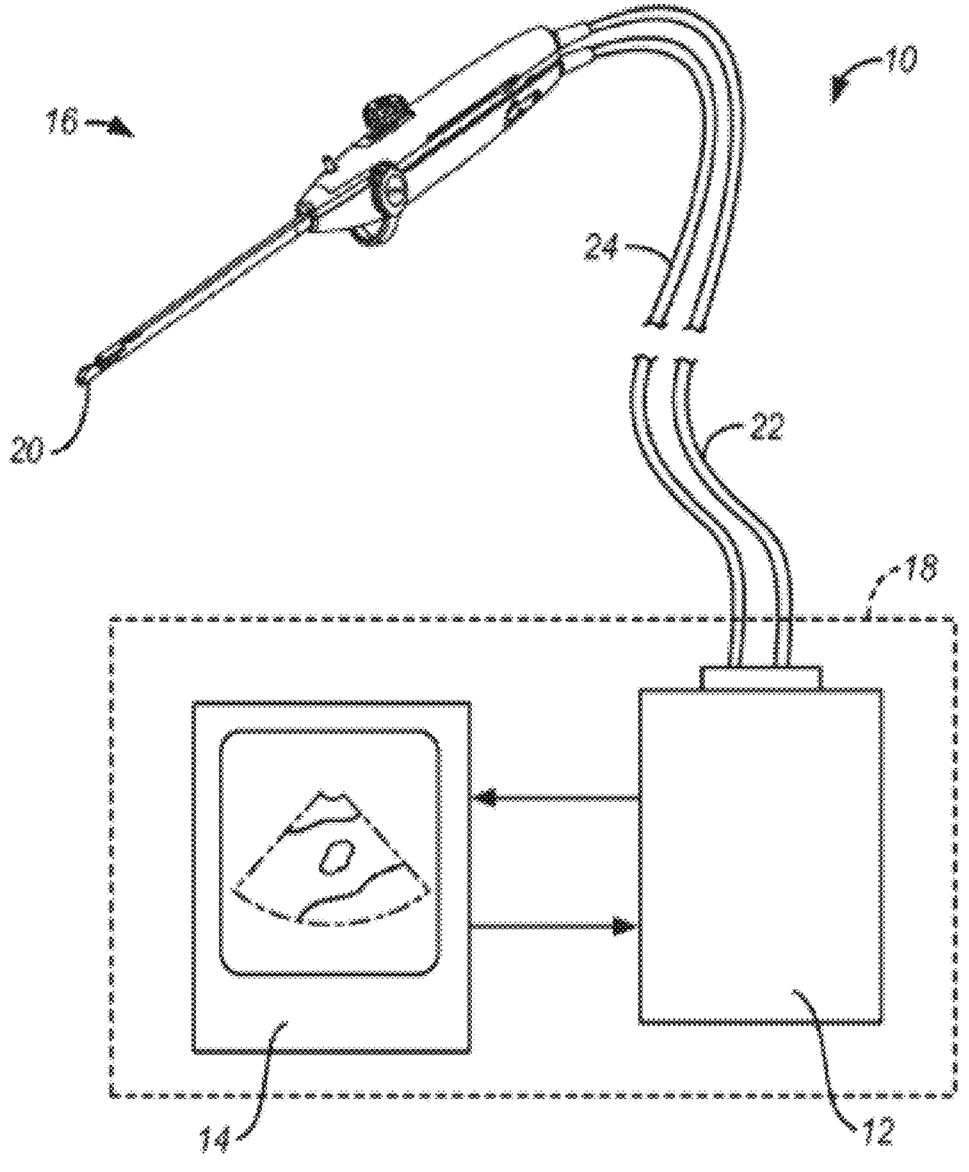
FIG. 1 is a schematic illustration of the system of the present disclosure comprising a system controller, an image display, and a treatment probe having a deployable needle structure and imaging transducer, in accordance with the principles of the present disclosure.

As illustrated in FIG. 1, a system 10 constructed in accordance with the principles of the present disclosure may include a system controller 12, an imaging display 14, and a treatment probe 16. The system controller 12 will typically be a microprocessor-based controller which allows both treatment parameters and imaging parameters to be set in a conventional manner. The display 14 will usually be included in a common enclosure 18 together with the controller 12 but could be provided in a separate enclosure. The treatment probe 16 may include an imaging transducer 20 which may be connected to the controller 12 by an imaging cord 24. The controller 12 may supply power to the treatment probe 16 via a treatment cord 22. The treatment probe 16 may also be in communication with the controller 12 via the treatment cord 22 such as to provide one or more of a control signal, a feedback signal, a position signal, or a status signal, to name a few. The controller 12 will typically further include an interface for the treating operator to input information to the controller 12, such as a keyboard, touch screen, control panel, mouse, joystick, directional pad (i.e., a D-pad), or the like. Optionally, a touch panel may be part of the imaging display 14. The energy delivered to the treatment probe 16 by the controller 12 may be radiofrequency (RF) energy, microwave energy, a treatment plasma, heat, cold (cryogenic therapy), or any other conventional energy-mediated treatment modality. Alternatively or additionally, the treatment probe 16 could be adapted to deliver drugs or other therapeutic agents to the tissue anatomy to be treated. In some embodiments, probe 16 plugs into an ultrasound system and into a separate radio frequency (RF) generator. An interface line connects the ultrasound system and the RF generator.

Figure 2:
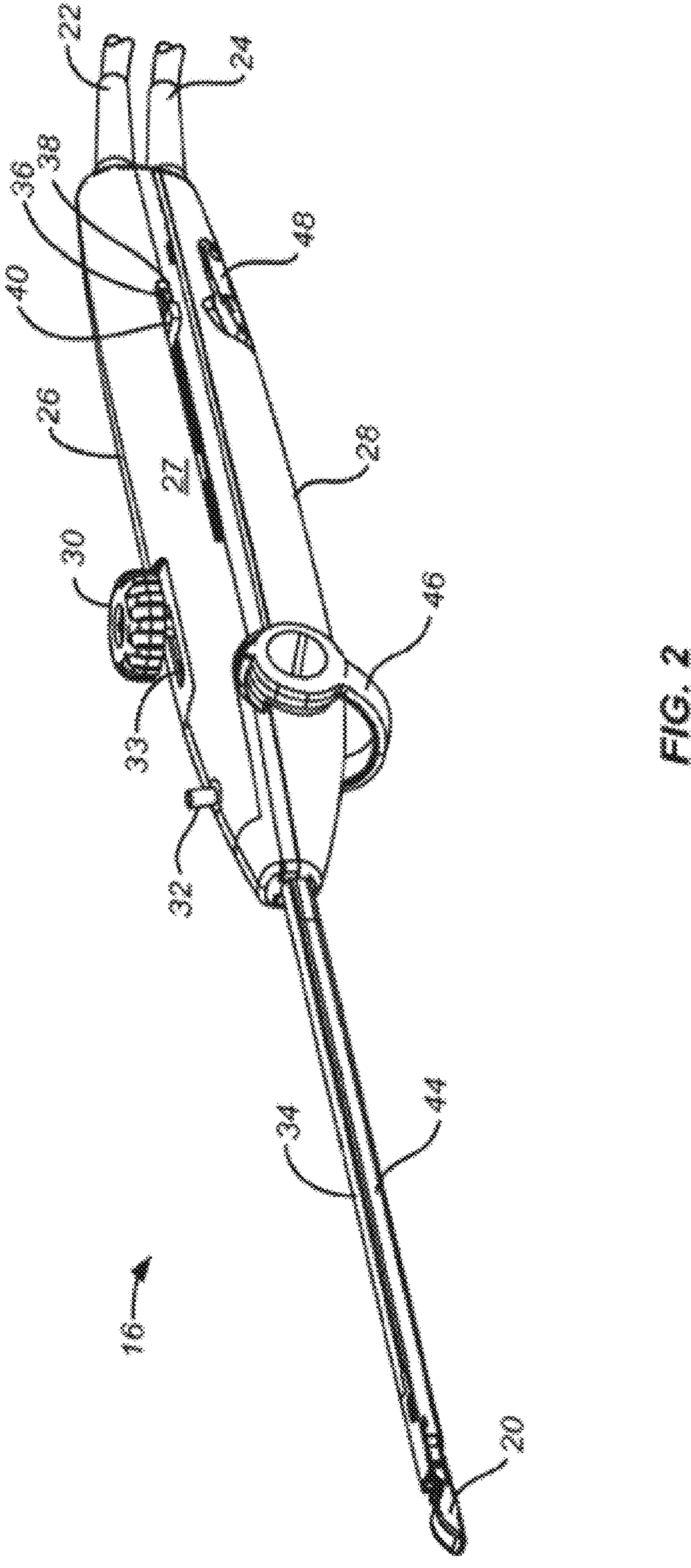
FIG. 2 is a perspective view of the treatment probe of the present disclosure, in accordance with the principles of the present disclosure.
Figures 3, 3A:
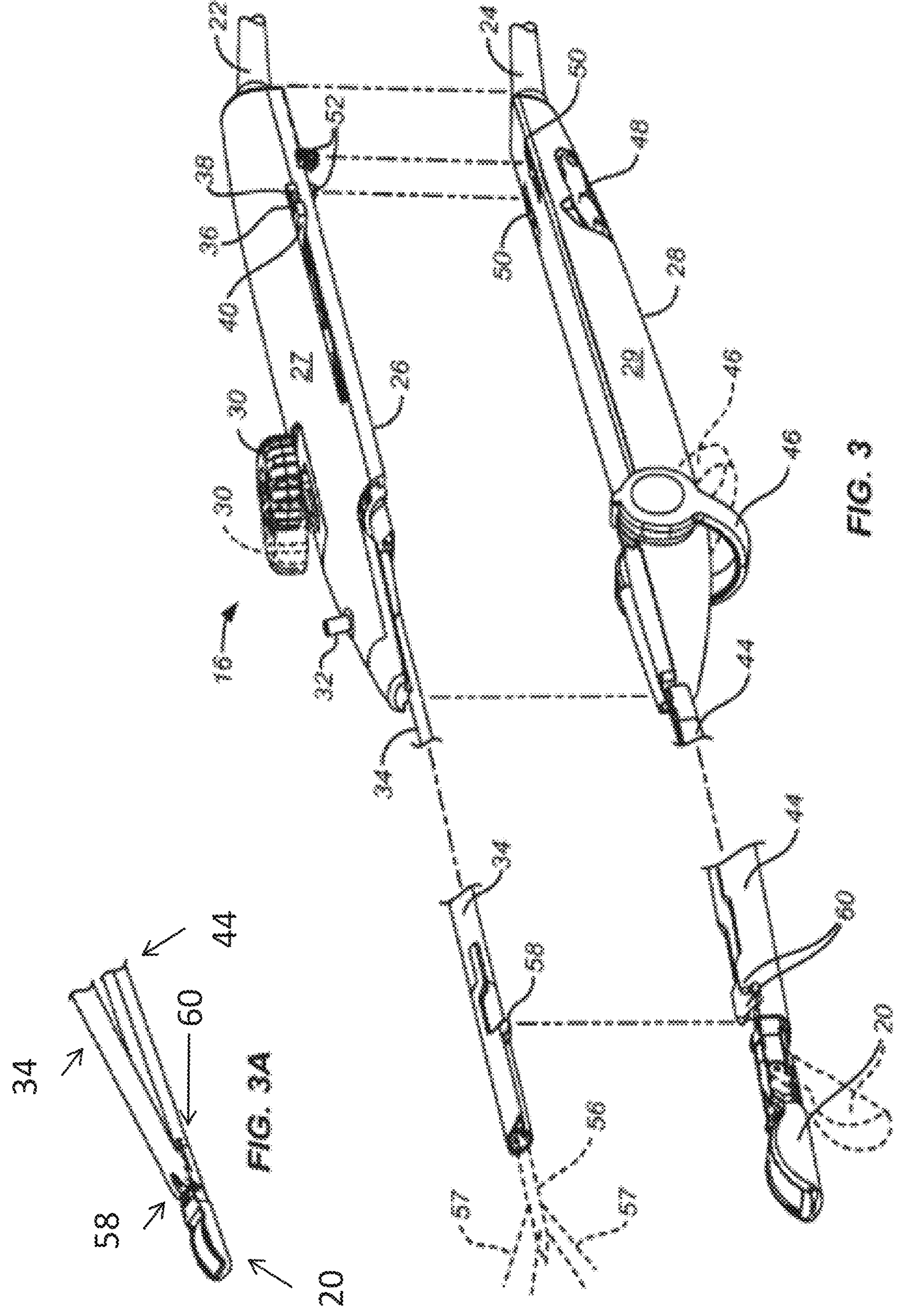
FIG. 3 is a view of the treatment probe of FIG. 2 illustrating an imaging component of the probe separated from a needle component with portions broken away and portions enlarged.
FIG. 3A illustrates a distal end of the needle component of the treatment probe of FIG. 2 being connected to a distal end of the imaging component.

Referring now to FIGS. 2 and 3, the treatment probe 16 may comprise a needle component 26 and an imaging component 28. The needle component 26 and the imaging component 28 may be constructed as separate units or assemblies which may be removably attached to each other for use. After use, the needle component 26 may be separated and will typically be discarded while the imaging component 28 may be sterilized for reuse. The treatment probe 16 is shown in its fully assembled configuration in FIG. 2 and is shown in its disassembled configuration in FIG. 3. In other embodiments of the present disclosure, the needle component 26 and the imaging component 28 could be combined in a single, integrated handle unit.

The needle component 26 may comprises a handle portion 27 having a control element 30 on its upper surface. The control element 30 may comprise a joystick, a directional pad (i.e., D-pad), or other user interface. While the control element 30 is illustrated as being on the handle portion 27, it is to be understood that it may be located anywhere on the treatment probe 16. For example, the control element 30 may be located anywhere along the handle portion 27 (e.g., near the distal end, the proximal end, or somewhere therebetween). As another example, the control element may be located on a side of the treatment probe (e.g., distally or proximal to the tine slide 40). As another example, the control element may be located on the imaging component 28. Optionally, the control element may face downwards. While particular examples have been given, the control element may be located on any components or elements of the present systems described throughout. For example, the control element may not be located on the treatment probe 16, but may be provided as part of, or be coupled to, the common enclosure 18, controller 12, and/or display. In some instances, the control element may be provided as a standalone unit that is coupled to the present systems via wired and/or wireless connections. The control element 30 may be in communication with the controller 12 to adjust the display 14, adjust treatment parameters, adjust the size and/or position of the targeting region and/or the safety region which are shown on the display 14, and/or perform other functions as will be described in more detail below. Optionally, the control element 30 may enable a user to draw marks or lines to identify or document a region of interest (e.g., during a procedure discussed herein). For example, the marks or lines may be made on a displayed image as the control element is manipulated to draw the marks. Optionally, the control element 30 may enable a user to interact with and/or control the controller 12 to access information sources (e.g., MRI images and/or clinical/Artificial Intelligent database) during procedures discussed herein, which may help improve the procedure quality. For example, access of the information sources may be done with menu items described in the present disclosure as the control element is manipulated to navigate the menu items. In some instances, the menu items may be accessed on a displayed image as the control element is manipulated to access the information sources (e.g., via the menu items).

The needle 56 may be deployed from the needle shaft 34, and the needle 56 and optional tines 57 together may form a needle structure which may be constructed, for example, as previously described in commonly owned U.S. Pat. Nos. 8,992,427, 8,206,300, and 8,262,574, the full disclosures of which are incorporated herein by reference.

The handle portion 27 of the needle component 26 may further include a fluid injection port 32 which allows saline or other fluids to be injected through the needle shaft 34 into a target region in the tissue being treated, such as the uterus. The needle handle 27 may also include a needle slide 36, a needle release 38, and a tine slide 40 which are used to deploy the needle 56 and tines 57. The needle slide 36 may be slid forward to advance the needle 56 and may be slid backward to retract the needle 56. The tine slide 40 may be slid forward to advance the tines 57 and may be slid backward to retract the tines 57. In some embodiments, the needle 56 and the tines 57 may be coupled to one or more servos within the body of the handle portion 27 which are configured to actuate the needle 57 and the tines 57, and the needle 56 and the tines 57 may be actuated by operating the control element 30 and/or the controller 12. In many embodiments, the needle 56 must be deployed first before the tines 57 can be deployed. The imaging cord 24 may be attachable at a proximal end of the handle portion 27 of the imaging component 28 for connection to the controller 12, as previously described.

The imaging component 28 may comprise a handle portion 29 and an imaging shaft 44. A deflection lever 46 on the handle portion 29 can be retracted in order to downwardly deflect the imaging transducer 20, as shown in broken line in FIG. 3. A needle component release lever 48 may be coupled to a pair of latches 50 which engage hooks 52 on a bottom surface of the handle portion 27 of the needle component 26. The needle component 26 may be releasably attached to the imaging component 28 by first capturing a pair of wings 58 (only one of which is shown in FIG. 3) on the needle shaft 34 beneath hooks 60 on the imaging shaft 44, as shown in FIG. 3A. A bottom surface of the needle handle portion 27 may then be brought down over an upper surface of the imaging handle portion 29 so that the hooks 52 engage the latches 50 to form a complete assembly of the treatment probe 16, where the handle portions together form a complete handle, for use in a procedure. After use, the needle component release lever 48 may be pulled in order to release the hooks 52 from the latches 50, allowing the handle portions 27 and 29 to be separated.

In use, as will be described in more detail below, the control element 30 may be used to both position (translate) and adjust the size of a virtual treatment region which is projected onto the display 14 of the system 10. The control element 30 may be pressed forward (up) and pressed backward (down) in order to translate the position of the treatment/safety region on the image, for example. The control element 30 may be pressed to the left and/or right to adjust the size of the boundary of the treatment/safety region. For example, the control element 30 may be pressed to the left to shrink the boundary while the control element 30 may be pressed to the right to enlarge the boundary. Once the virtual boundaries of the treatment/safety region have been set on the real-time image, the needle and tines may be automatically advanced to the corresponding deployment positions by moving the needle slide 36 and tine slide 40 until their movement is arrested by the user as recommended by the stops. The position of the treatment/safety region may also be dependent on the location at which the operator holds the treatment probe 16 within the target tissue. Thus, advancement of the needle 56 and tines 57 using the slides 36 and 40 will result in the proper placement of the needle and tines within the target tissue only if the treatment probe position is held steady from the time the boundaries are set until advancement of the needle/tines is completed.

In preferred embodiments, the control element 30 may also be manipulated to adjust the length of and/or power delivery during a treatment protocol. For example, the control element 30 may be pressed to select a different control menu from one for the adjustment of the boundaries, and one of the selectable menus may allow the power delivery parameters to be adjusted such as by pressing up/down to adjust the time length for power delivery and pressing left/right to adjust the amount of power delivered. Another menu may comprise a menu for deploying the needle 56 and the tines 57 by operating the control element 30, such as in embodiments where the needle 56 and the tines 57 are articulated using one or more servos within the handle component 27 of the needle component 26. Yet another menu may be selected to allow the control element 30 to move a cursor on the display 14. Thus, the control element 30 may be used to virtually size the treatment/safety region based not only on the degree to which the tines have been advanced, but also the amount of energy which is being delivered to the target tissue.

Optionally, the control element may also be manipulated to make mark ups (e.g., on a display). For example, during a procedure or treatment described herein, a user may utilize the control element 30 to mark, identify, and/or document a region of interest. The marking, identifying, and/or documenting may in some instances be implemented with aid of the display 14. For example, the control element 30 may be utilized to mark (e.g., with dots, lines, shapes, circles, polygons, etc.) a region of interest that is displayed on the display unit (e.g., in real time during a procedure). Marks made may be saved or recorded in some instances for further use. Optionally, the marking, identifying, or documenting may be implemented by the control element by selecting another menu, substantially as described above. Alternatively, the marking may be available to be implemented by the control unit while having selected a given menu described above as further described below.

Optionally, the control element may also be manipulated to access information sources. The information sources may in some instances be accessed to aid and/or improve the procedures described herein. The information sources may include, but are not limited to, magnetic resonance imaging (MRI) images, clinical databases, and/or artificial intelligence databases. For example, during a procedure or treatment described herein, a user may utilize the control element 30 to access an information source. The accessing may in some instances be implemented on the display 14. For example, the control element 30 may be utilized to access an information source which may be utilized to display relevant information on the display 14. Optionally, accessing of the information source may implement algorithms that automatically or semi-automatically analyze information on the display to help improve the procedures or treatments described herein. Optionally, the accessing of the information sources may be implemented by the control element by selecting another menu, substantially as described above. Alternatively, the accessing of the information sources may be available to be implemented by the control unit while having selected a given menu described above as further described below.

In some instances, a given menu may be provided (or selected) for the control element 30 to provide a plurality of the functionalities described herein. For example, the control element 30 may provide two, three, four, five, six, seven, eight, nine, ten or more of the functionalities (e.g., position (translate) and adjust the size of a virtual treatment region, adjust the length of and/or power delivery during a treatment protocol, deploy the needle and the tines, move a cursor on the display, make mark ups, access information sources, etc.) within a single menu. For example, the control element 30 may comprise various mechanisms (e.g., movable, rotatable, depressible, etc.). A first mechanism may control a first functionality while a second mechanism may control a second functionality. For example, moving the control element may position and/or adjust a size of a virtual treatment region while rotation the control element may adjust a length of and/or power delivery during a treatment protocol. As another example, moving the control element may allow movement of a cursory on the display while depressing the control element may allow the control element to draw marks or lines to identify or document a region of interest.

Figure 4:
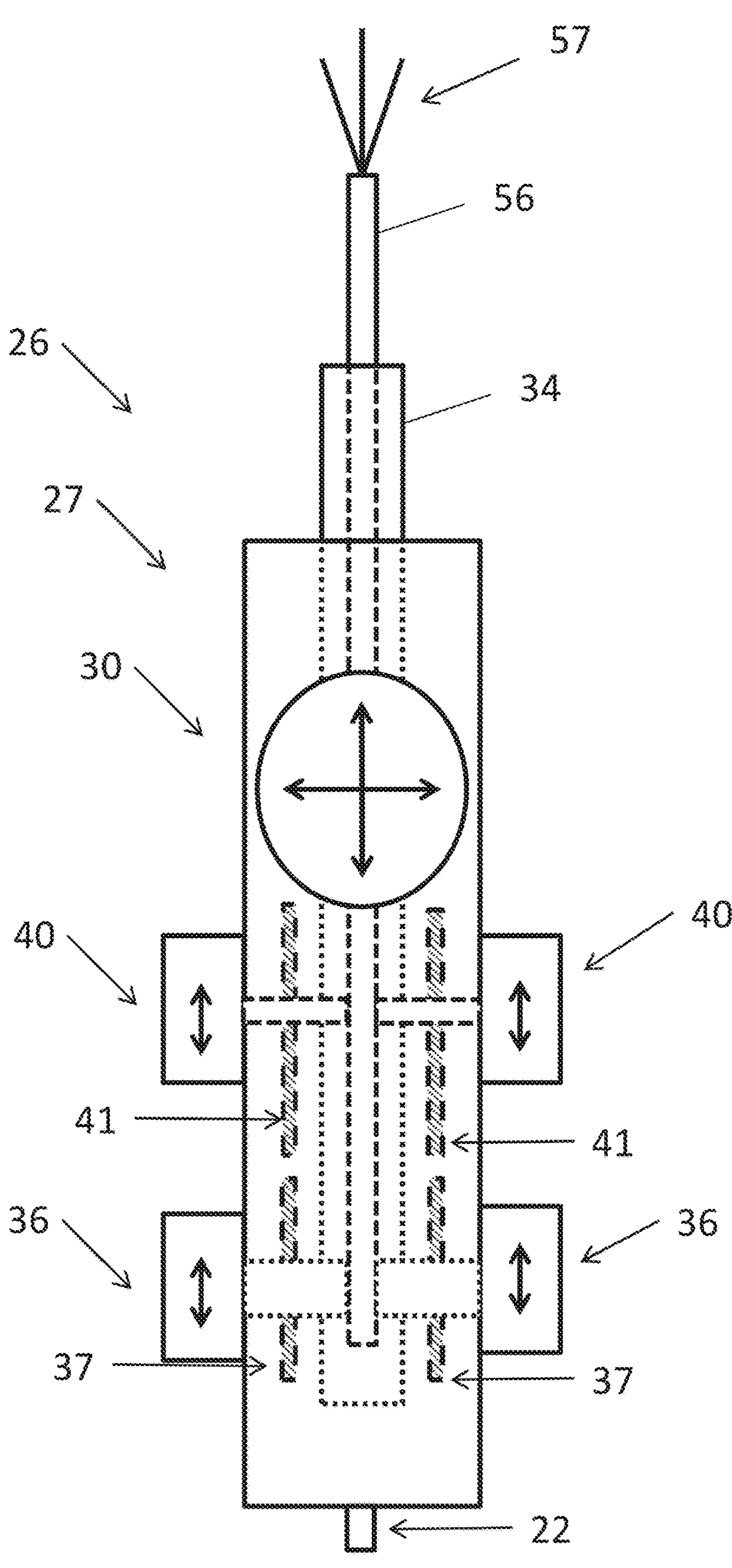
FIG. 4 illustrates a schematic view of the treatment probe of the present disclosure, in accordance with the principles of the present disclosure.

FIG. 4 shows a schematic illustration of the needle component 26 of the treatment probe 16. As shown in FIG. 4, the needle component 26 may comprise one or more needle position sensors 37 and one or more tines position sensors 41. The needle position sensor(s) 37 may be coupled to a handle end portion of the needle deployment shaft 34. Advancement and retraction of the needle 56 by the slide 36 can thereby be tracked by the needle position sensor(s) 37. The needle position sensor(s) 37 may generate a position signal for the needle deployment shaft 34 which may be sent to the controller 12 through the treatment cord 22 and from which the position of the needle 56 can be determined. Likewise, the tines position sensor(s) 41 may be coupled to a handle end portion of the tines deployment shaft disposed within the needle deployment shaft 34. Advancement and retraction of the tines 57 by the slide 40 can thereby be tracked by the needle position sensor(s) 37. The tines position sensor(s) 41 may generate a position signal for the tines deployment shaft which may be sent to the controller 12 through the treatment cord 22 and from which the position of the tines 56 can be determined. The needle position sensor(s) 37 and the tines position sensor(s) 41 may comprise any type of position sensor such as a linear encoder, a linear potentiometer, a magnetic sensor, a linear variable differential transformer (LVDT) sensor, a rheostat sensor, or a pulse encoder, to name a few. The positions of the needle 56 and/or tines 57 may be tracked in real time by the position sensors 37, 41 and the controller 12. The calculated treatment and/or safety boundaries may be displayed and adjusted on the display unit 14 as the position of the needle 56 and tines 57 are tracked and optionally updated if moved. Alternatively or in combination, the needle 56 and tines 57 may be translated using one or more servo motors which may additionally provide position information for the needle 56 and the tines 57.

The operator may adjust the control element 30 to locate the boundaries of the treatment/safety region as desired to be shown on the visual display 14.

A particular advantage of this method and system is that the operator can manipulate the treatment/safety boundaries over the target anatomy by either moving the boundaries relative to (or within) the real-time image by manipulating (pressing forward/backward, left/right) the control element 30 or moving the entire real-time image with respect to the target anatomy by manipulating the entire treatment probe 16 in order to get the treatment boundary over the tumor and keeping the safety boundary away from sensitive anatomy. So, before the operator advances any needles into the patient tissue, they can confirm in advance using the virtual targeting interface that the ablation will be effective and safe.

Figure 5:
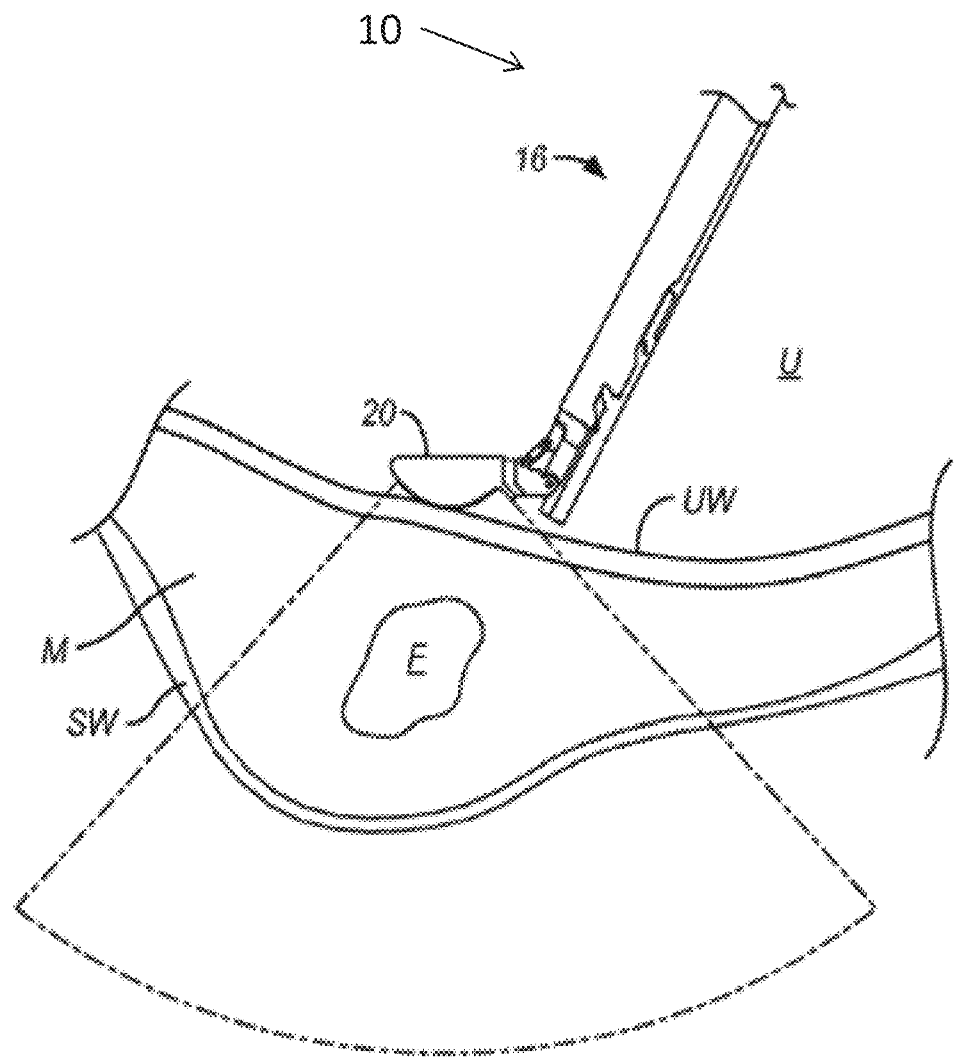
FIG. 5 illustrates a distal portion of the treatment probe introduced into a uterine cavity to image a fibroid in the myometrium, in accordance with the principles of the present disclosure.

Referring now to FIG. 5, the system 10 of the present disclosure can be used to treat a fibroid F located in the myometrium M in a uterus U beneath a uterine wall UW (the endometrium) and surrounded by the serosal wall SW. The treatment probe 16 can be introduced transvaginally and transcervically (or alternately laparoscopically) to the uterus, and the imaging transducer 20 deployed to image the fibroid within a field of view indicated by the broken lines.

The system 10 may allow the operator to draw virtual boundaries to separate the anatomical features, for example, the serosal wall SW and myometrium M, and the fibroid F and the myometrium M. The system 10 may allow the operator to label anatomical features. These boundaries and/or labels may be shown on the display 14. In many embodiments, the boundary and/or labeling data may be saved to a training set of data, and the training set of data may be used to train a classifier model. Once trained, the classifier model may be incorporated into the system 10, and the system 10 may automatically recognize anatomical structures and/or boundaries and suggest anatomical boundaries and/or labels for the ultrasound image, streamlining the workflow. In many embodiments, the system 10 may first identify and suggest anatomical structures and boundaries and provide labels and markings for these anatomical structures and boundaries, respectively, before confirming the labels and boundaries with the operator. The system 10 may provide the operator options to update the suggested anatomical boundaries and/or labels, and the updated image may be added to the training set to update the classifier model.

Figure 16:
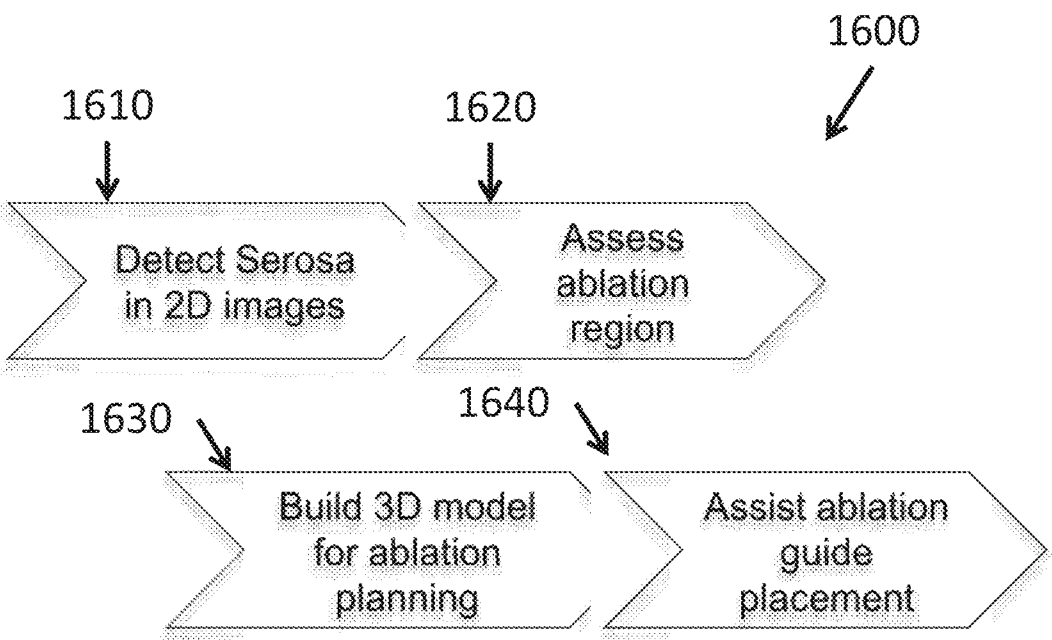
FIG. 16 illustrates a flow chart of an image guided method of treating tissue, in accordance with the principles of the present disclosure.
Figure 17:
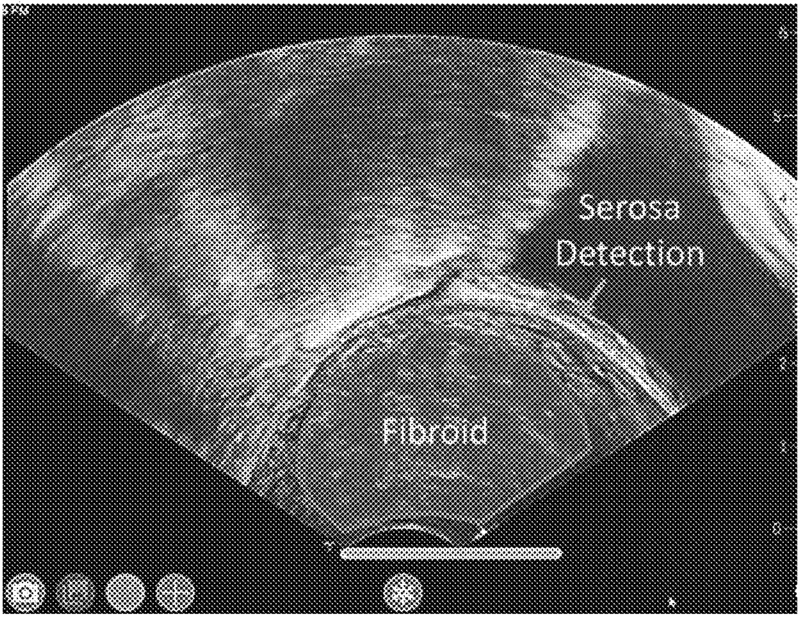
FIGS. 17-19 illustrate exemplary ultrasound images provided with image labeling and anatomical boundaries, in accordance with the principles of the present disclosure.
Figure 18:
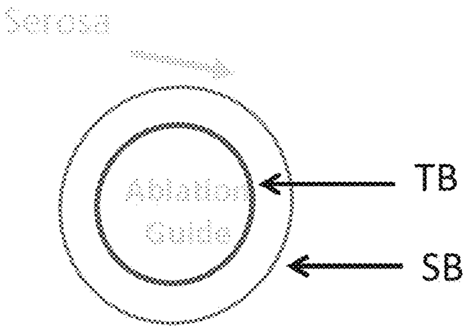

Referring to FIG. 16, the present disclosure may provide a method 1600 for image guided surgery. In a step 1610, the classifier model may detect the serosa or serosal wall SW in one or more two-dimensional (2D) image, such as an intra-uterine ultrasound image. Other anatomical features and boundaries may be detected, labeled and/or marked, and placed on this display, such as for the serosa, the myometrium, other fibroid(s), the uterine wall, the bladder wall, or the bladder. FIG. 17, for instance, shows an intra-uterine ultrasound image in which a fibroid is identified and labeled (Fibroid), and the serosal wall is detected, and a boundary is placed for the serosal wall and marked (Serosa or Serosa Detection). In a step 1620, an ablation region may be assessed, such as by the classifier model identifying, placing boundaries around, and labeling one or more uterine fibroids. In a step 1630, a three-dimensional (3D) model may be built for ablation planning, such as by compiling a plurality of the 2D images. In a step 1640, an ablation guide is provided to assist placement of the treatment element(s), for example, the needle 56 and tines 57. For example, the ablation guide may include a suggested treatment boundary TB and safety boundary SB as shown in the intra-uterine image of FIG. 18.

The classifier model may comprise a machine learning algorithm, such as a convolutional deep learning network. Alternatively or in combination, the classifier model may be one or more of a binary tree, a random forest, a decision tree, a plurality of decision trees, a plurality of decision trees with controlled variance, a multinomial logistic regression, a naïve Bayes classifier, a linear classifier, an ensemble of linear classifiers, a boosting algorithm, a boosting algorithm trained with stochastic gradient descent, a boosting algorithm trained with stochastic gradient descent, a boosting algorithm comprising training data weighting, a boosting algorithm comprising updating training data weighting, or a boosting algorithm comprising updating misclassified training data with higher weights.

Although the above steps show method 1600 of image guided surgery according to many embodiments, a person of ordinary skill in the art will recognize many variations based on the teaching described herein. The steps may be completed in a different order. Steps may be added or deleted. Some of the steps may comprise sub-steps. Many of the steps may be repeated as often as beneficial to the method.

Figure 6A:
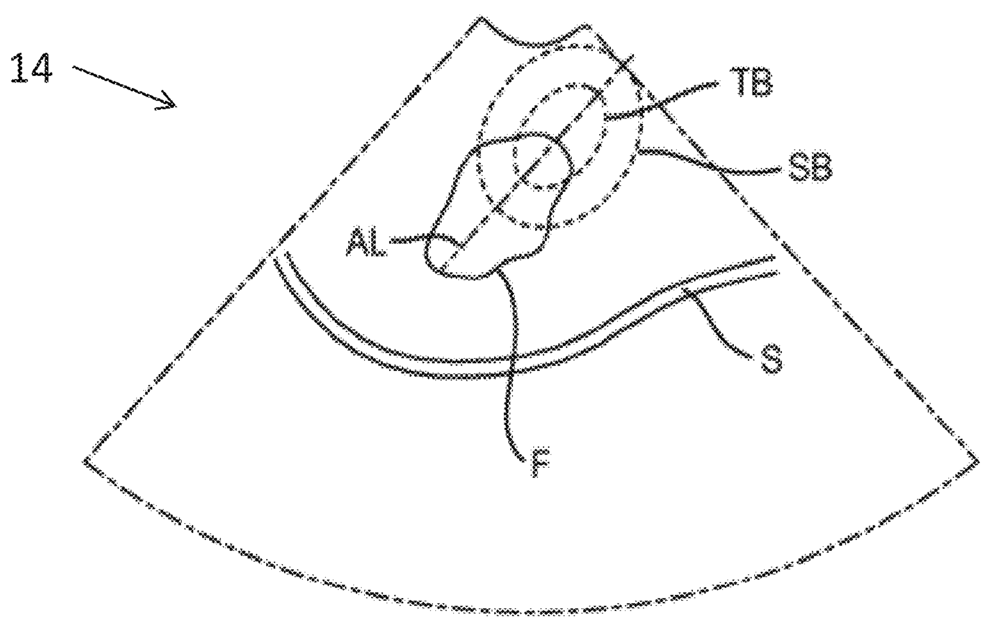
FIGS. 6A, 7A, 8A, 9A, 10A, and 11A illustrate "screen-shots" of the real-time image display as the treatment and safety boundaries are being adjusted using the treatment probe, in accordance with the principles of the present disclosure.
Figure 6B:
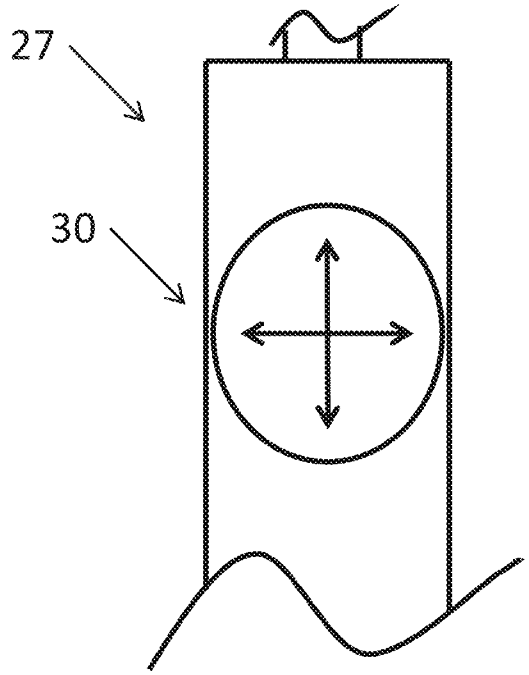
FIGS. 6B, 7B, 8B, 9B, 10B, and 11B illustrate manipulation of the handle which corresponds to the repositioning of the projected images of the treatment and safety boundaries on the real-time images of FIGS. 10A-15A.
Figure 7A:
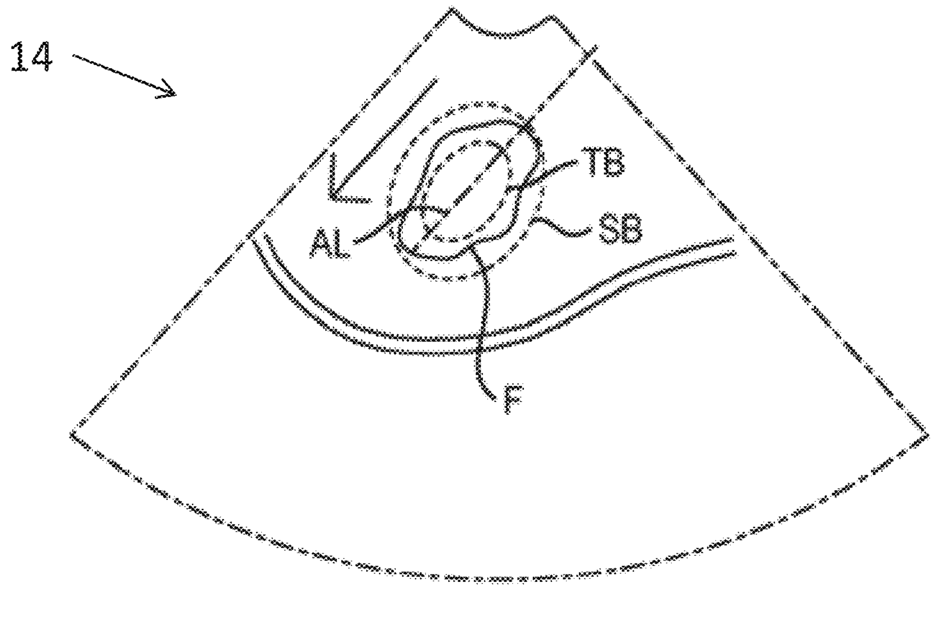
Figure 7B:
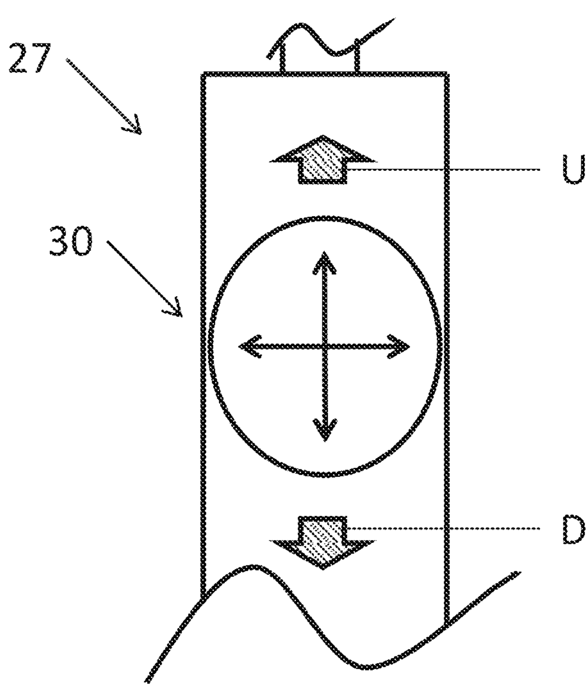

Once the fibroid is located on the display 14, as shown in FIG. 6A, the control element 30 on the handle component 27 can be used to locate and size, or re-locate and re-size, both the treatment boundary TB and the safety boundary SB. Initially, as shown in FIG. 6A, the virtual boundary lines TB and SB may neither be positioned over the fibroid nor properly sized to treat the fibroid, and the control element 30 may be in a neutral position as shown in FIG. 6B. Alternatively, the virtual boundary lines TB and SB may be suggested by the ablation guide according to the method 1600 as described above. Prior to actual needle and tine deployment, the operator may want to both position and size, or re-position and re-size the boundaries TB and SB for proper treatment. As the imaging transducer 20 may already be positioned against the uterine wall UW, the only way to advance the treatment and safety boundaries TB and SB is to move the boundaries forward by manipulating the control element 30, such as by pressing the control element 30 forward in the direction of arrow U as shown in FIG. 7B. This manipulation may cause the treatment and safety boundaries TB and SB to move forwardly along the axis line AL. This manipulation may also cause the virtual boundaries on the real-time image display 14 to move over the image of the fibroid, as shown in FIG. 7A. If the treatment and safety boundaries TB and SB need to be retracted, the control element 30 may be manipulated such as by pressing the control element 30 backward in the direction of arrow D as shown in FIG. 7B.

Figure 8A:
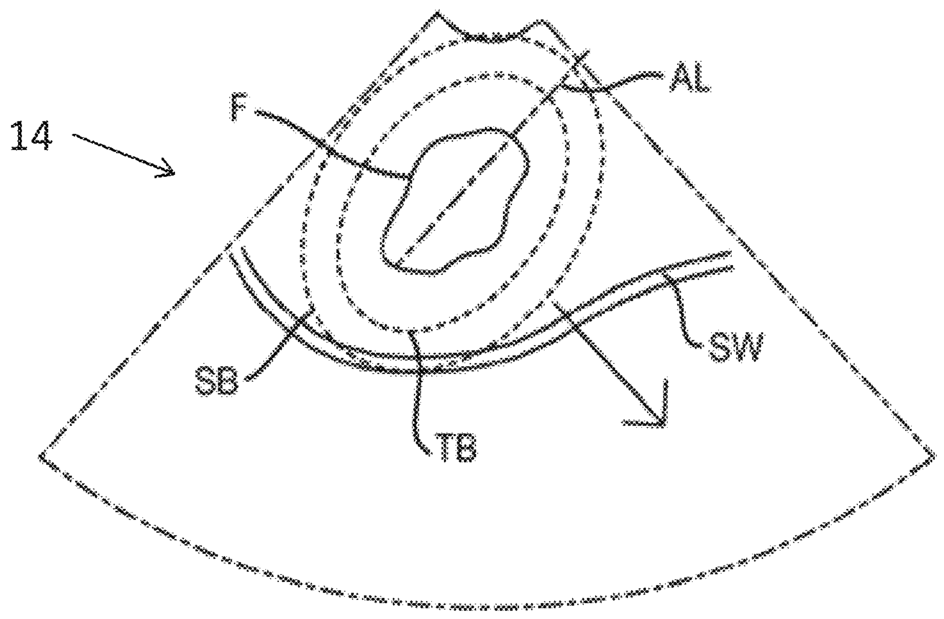
Figure 8B:
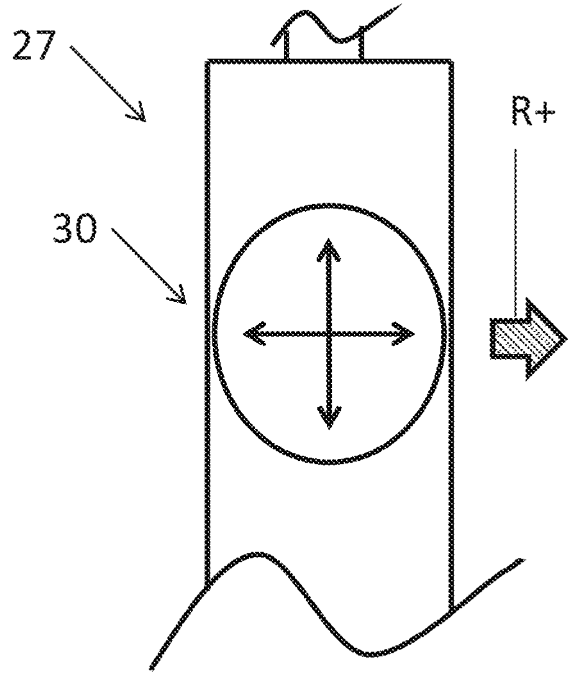
Figure 9A:
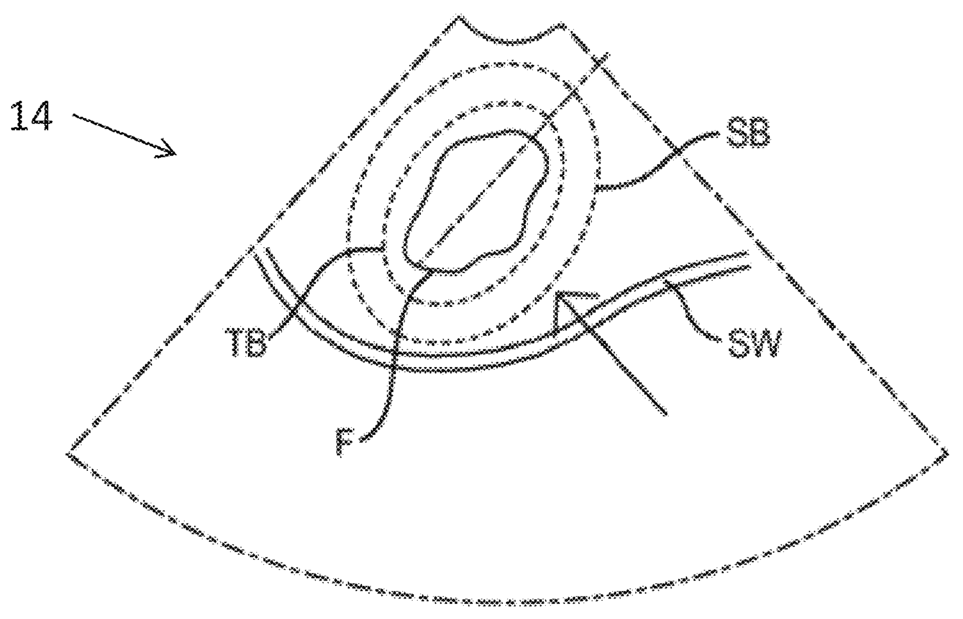
Figure 9B:
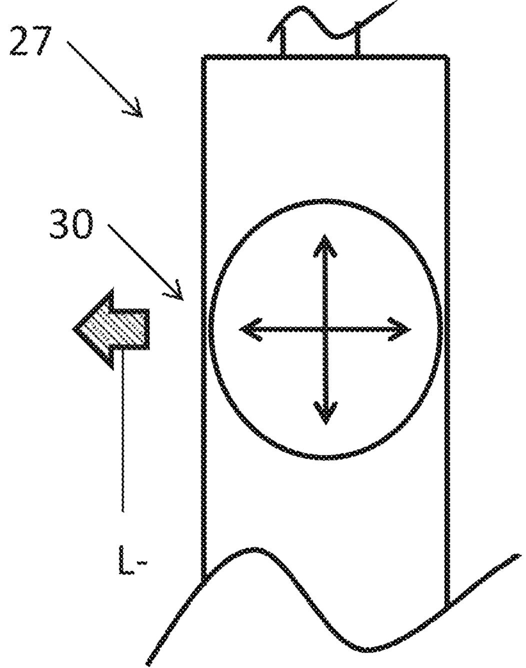

As shown in FIG. 7A, however, the size of the treatment boundary TB may be insufficient to treat the fibroid since the boundary does not extend over the image of the fibroid. Thus, it may be necessary to enlarge the treatment boundary TB by manipulating the control element 30, as shown in FIG. 8B, such as by pressing the control element 30 to the right in the direction of arrow R+. This may enlarge both the treatment boundary TB and the safety boundary SB, as shown in FIG. 8A. While the enlarged virtual treatment boundary TB may now be sufficient to treat the fibroid, the safety boundary SB has extended over the serosal wall SW, as also shown in FIG. 8A. Thus, there may be a risk that the treatment would affect more sensitive tissue surrounding the uterus, and it may be necessary that the virtual safety boundary SB be retracted by again manipulating the control element 30 in an opposite direction, such as by pressing the control element 30 to the left in the direction of arrow L– as shown in FIG. 9B. This manipulation may reduce the size of both the safety and treatment boundaries SB and TB, as shown in FIG. 9A, and the operator may have confirmation that the treatment may be effective because the treatment boundary TB completely surrounds the fibroid on the real-time image display, and that the treatment will be safe because the safety boundary SB is located within the myometrium M and does not cross the serosal wall SW on the real-time image display.

Figure 10A:
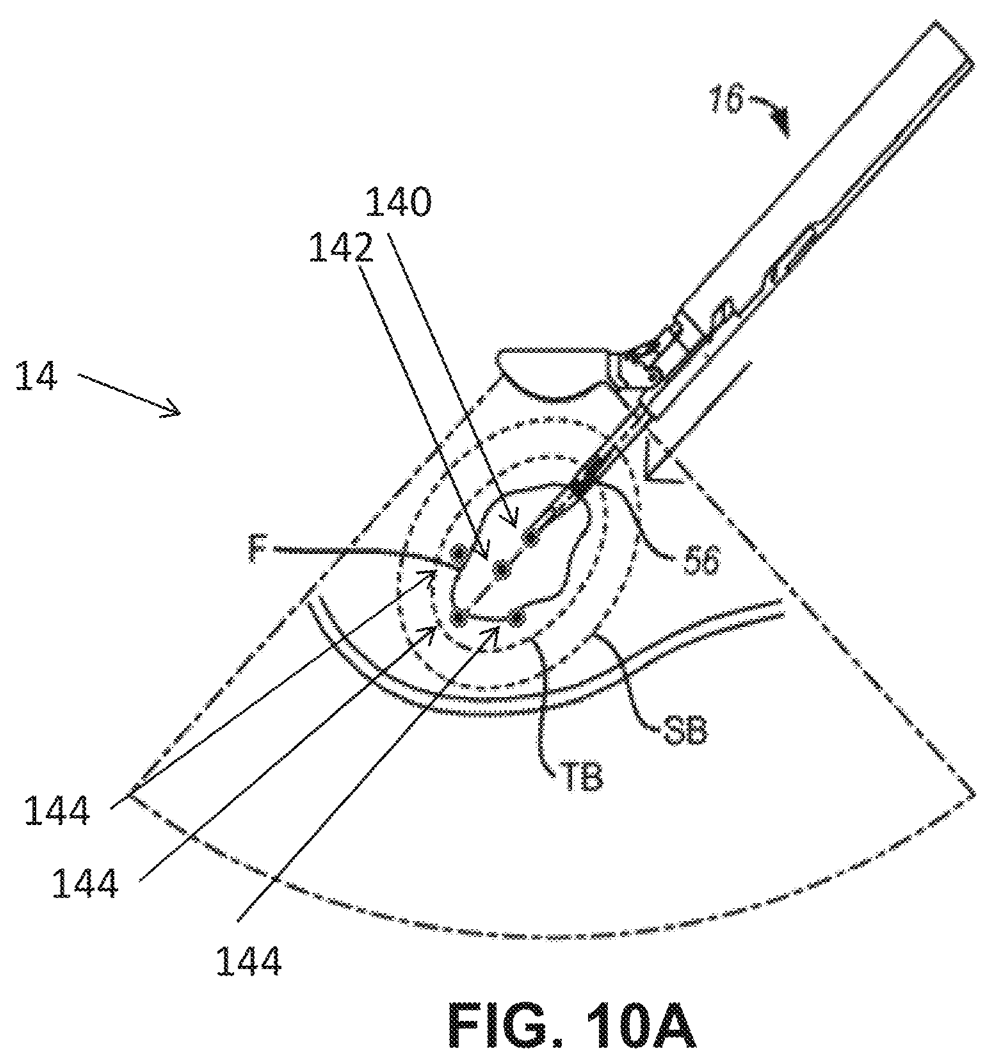
Figure 10B:
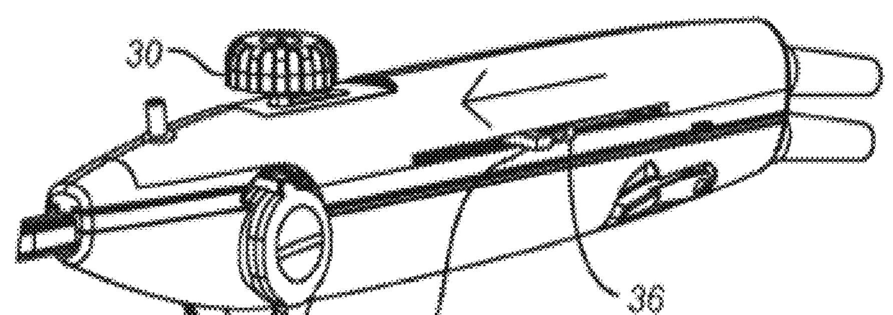

While holding the treatment probe 16 steady, the operator may then advance the needle slide 36, as shown in FIG. 10B, causing the needle 56 to extend into the fibroid F, as shown in FIG. 10A. The illustration in FIG. 10A includes a representation of the treatment probe 16 which may correspond to the physical probe which is present in the patient. The remainder of FIG. 10A corresponds to the image present on the target display 14. The treatment and safety boundaries TB, SB may determine a virtual stop indicator or fiducial 142 for the needle 56. The target display 14 may include a position indicator 140 for the needle 56, in many cases the tip of the needle 56. In some cases, the positions of the virtual needle stop indicator or fiducial 142 may correlate with the size and position of the treatment and safety boundaries TB and SB. In other cases, the positions of the virtual needle stop indicator or fiducial 142 may be adjusted independently with respect to the treatment and safety boundaries TB and SB. The needle 56 may be advanced until the needle position indicator 140 overlaps the virtual needle stop fiducial 142. In many embodiments, the virtual needle stop fiducial 142 may be "locked" with the needle position indicator 140 after the overlap occurs. In prior treatment probes, the advancement of the needle structure is halted with a mechanical stop which cannot be adjusted after the needle structure has been fully advanced. In the many embodiments, the virtual needle stop fiducial 142 is a virtual guide for stoppage of the needle structure and can be further adjusted even after the needle 56 has been advanced to the initial position of the virtual needle stop fiducial 142.

Figure 19:
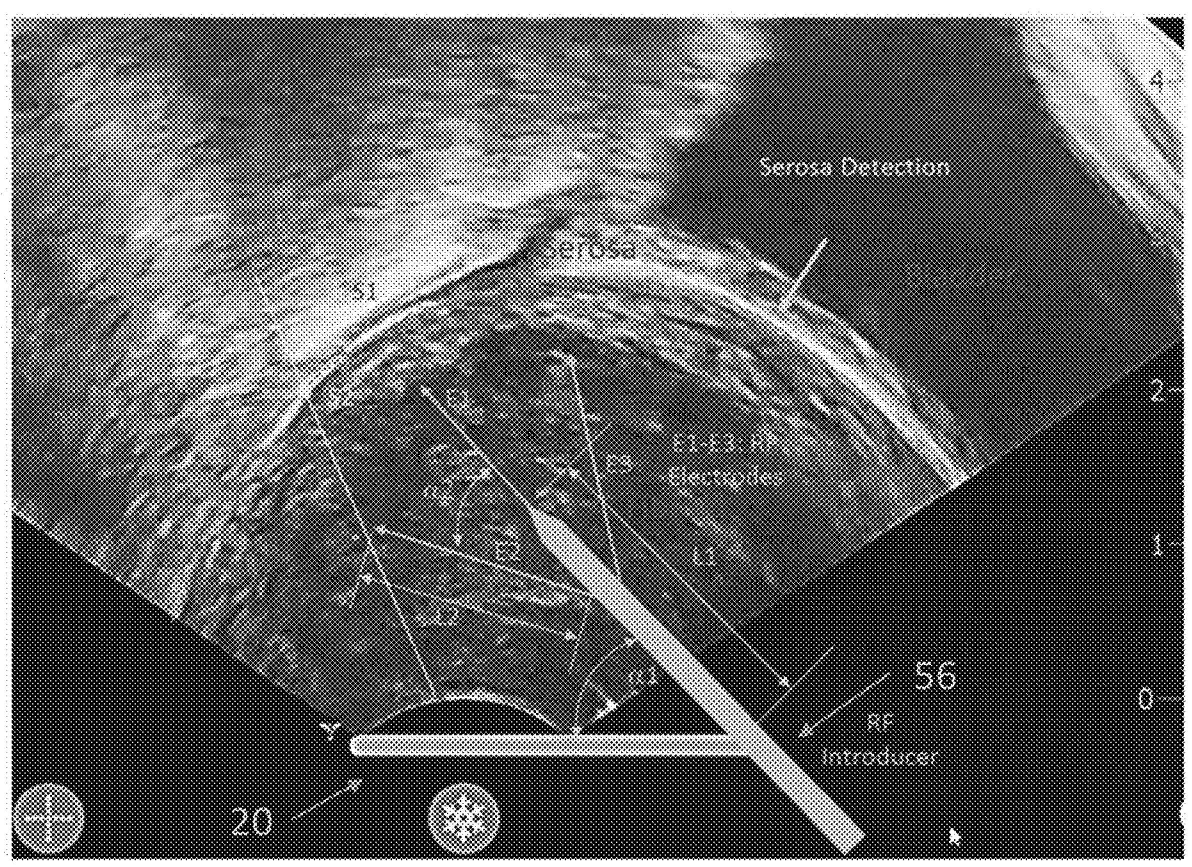

Referring to FIG. 19, when the needle 56 is extended into the fibroid F, the needle 56 may be shown with the intra-uterine ultrasound image with suggested anatomical labels and boundaries. For instance, in FIG. 19, the bladder, serosa, and fibroid are labeled (Bladder, Serosa, and Fibroid, respectively), and a boundary is placed at the serosa wall (Serosa Detection). With the needle 56 (also referred to as RF Introducer) in position, the distance from the serosa to the surface of the imaging transducer 20 can be known. The mechanical coupling between the needle 56 and the imaging transducer 20 can provide a space coordination, for instance, a known angle $\alpha$1, between the needle 56 and the surface of the imaging transducer 20, as well as a known distance L1 between the coupling and the end of the needle 56. The needle position sensor 37 and the tine position sensors 41 can be used to predict the positions of the needle 56 and the tines 57 as described herein. As shown in FIG. 19, the tines 57 may extend to pre-determined lengths E1, E2, and E3, with a pre-determined angle $\alpha$2 between the tines. S1 may be the safety margin based on the position of the needle 56 and the tines 57 as well as estimated from ablation parameters as described further herein. S2 may be the distance between the surface of the imaging transducer 20 and the serosal wall as identified by the classifier model. The suggested safety margin or boundary, as well as the suggested treatment boundary may be modified and discarded by the operator. The system 10 may display warning messages when the operator manually places the guides (e.g., treatment boundary, safety boundary, fiducials for the positions of the needle and tines) and/or fails to any safety rule.

Figures 11A, 11B:
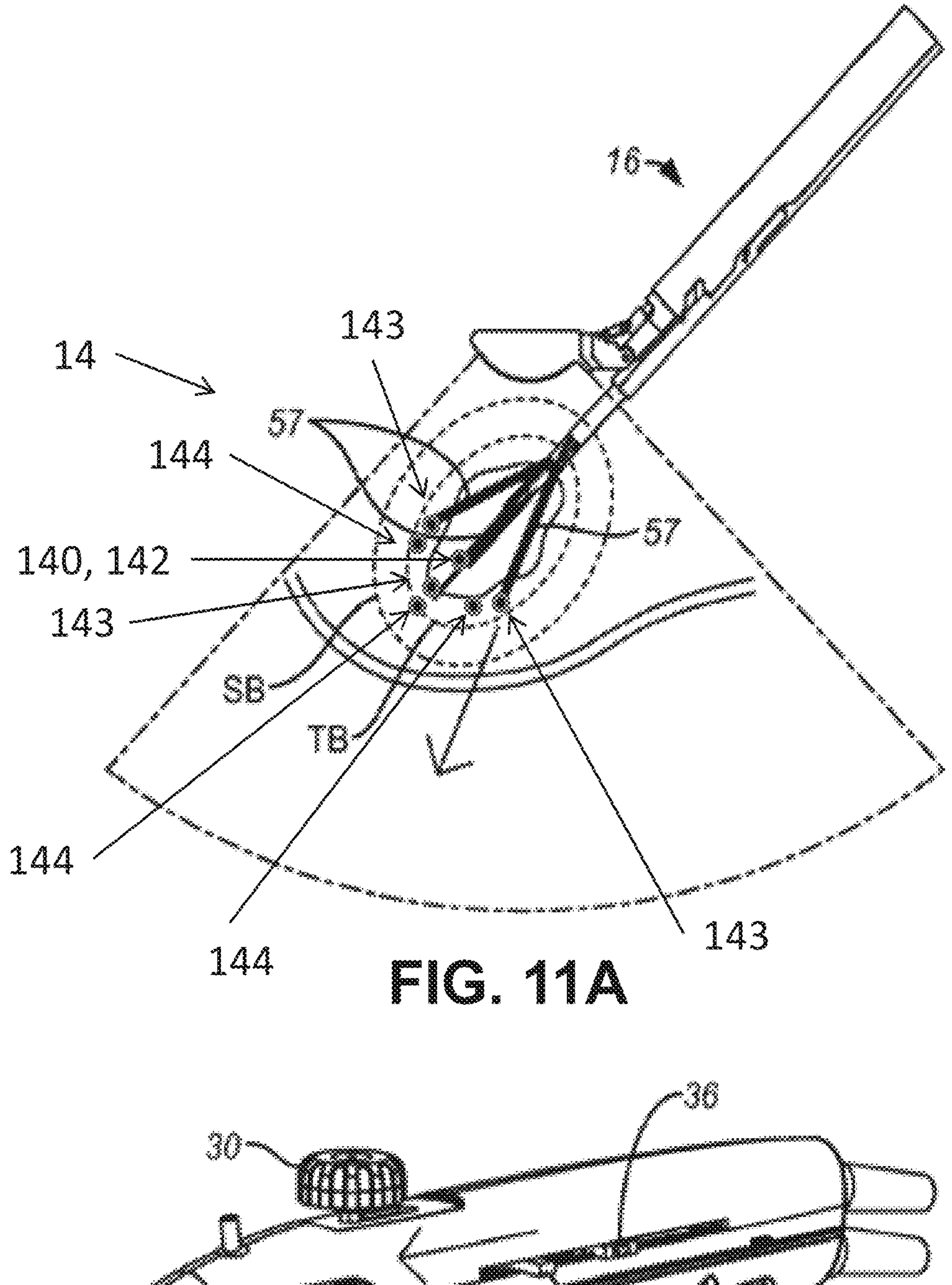

Referring back to FIG. 11A, the target display 14 may include position indicators 143 for the tines 57, in many cases the tip of the tines 56. The treatment and safety boundaries TB and SB may also determine a plurality of virtual stop indicators or fiducials 144 for the tines 57 as shown in FIG. 10A. In many embodiments, the position of the tines may be determined from the needle position sensor 37 to be shown by the tine position indicators 143 on the target display 14 as shown in FIG. 11B. In some cases, the positions of the virtual tine stop indicators or fiducials 144 may correlate with the size and position of the treatment and safety boundaries TB and SB. In other cases, the positions of the virtual tine stop indicators or fiducials 144 may be adjusted independently with respect to the treatment and safety boundaries TB and SB. In prior treatment probes, the advancement of the plurality of tines is halted with a mechanical stop which cannot be adjusted after the plurality of tines has been fully advanced. In many embodiments, virtual tine stop fiducials 144 are virtual guides for stoppage of the plurality of tines and can be further adjusted even after the plurality of tines 57 have been advanced to the initial positions of the virtual tine stop fiducials 144.

After the needle 56 has been fully deployed as indicated by the overlap of the needle position indicator 140 and the virtual needle stop fiducial 142, the tines 57 may be deployed by advancing the tine slide 40, as shown in FIG. 11B, until the tine position indicators 143 overlap with the virtual needle stop fiducials 144. Optionally, the treatment probe 16 may be rotated about a central axis (typically aligned with the axis of the needle 56) to confirm the treatment and safety boundaries TB, SB in all planes of view about the fibroid. Display 14 may show the position of the treatment and safety boundaries TB and SB in real time relative to the target fibroid F and serosal wall SW. The tines may be configured as shown in FIG. 11A, and power can be supplied to the tines 57 (and optionally the needle 56) in order to achieve treatment within the boundary depicted by the virtual treatment boundary TB. Again, FIG. 11A may mix both the virtual image which would be present on the display 14 as well as the physical presence of the treatment probe 16.

Figures 12A, 12B, 12C, 12D:
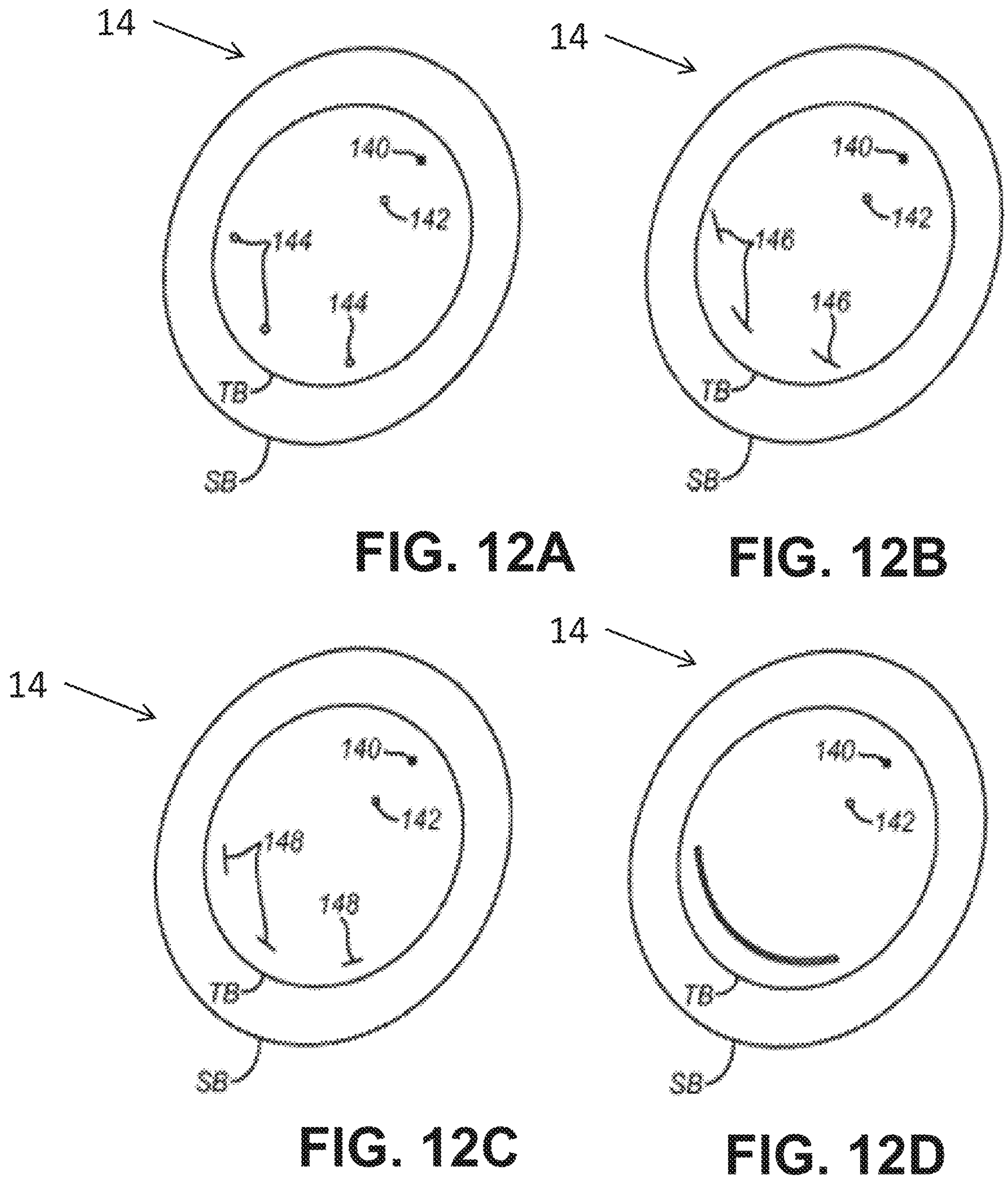
FIGS. 12A, 12B, 12C, and 12D illustrate the provision of fiducials or markers on the real-time image, where the fiducials or markers correspond to needle tip locations.

Referring now to FIG. 12A through 12D, the controller 12 can be programmed to display fiducials or markers on the image display 14, where the fiducials or markers represent particular locations on the "virtual" needle and/or tines. For example, as shown in FIG. 12A, marker 142 may represent a desired position on the needle 56, for example, the location to where a tip of the needle 56 may be intended to advance to and from which the tines are intended to diverge from. An additional marker 140 may be provided which represents the actual tip of the needle 56 in real time. A plurality of additional tine markers 143 may represent the tips of the tines, as shown in FIG. 11A. The use of such fiducials or markers may help the operator confirm that the actual needle 56 and tines 57 are deployed correctly. The operator should be able to observe the real-time images of the actual needle 56 and tines 57 during deployment, and the associated tips should move until the needle tip reaches virtual needle marker 142, as indicated by an overlap of needle markers 140 and 142, and the tine tips hit markers 144, as indicated by an overlap of tine markers 143 and 144 (or alternatively with the alternative targets 146 and 148 in FIGS. 12B-12D as described below).

FIG. 12B is similar to FIG. 12A, except that the fiducials representing the tips of the tines 57 are depicted as arcs 146 which represent a range of possible positions for the distal tips of each tine. Such additional information may be useful for the operator when determining both adequacy of treatment and safety risks. As shown in FIG. 12B, each arc has a radius equal to the theoretical electrode deployment length. As shown in FIG. 12C, arcs 148 all have the same radius measured from the origin located at the tip 142. Finally, in FIG. 12D, the arcs of FIG. 12C are joined into a continuous arc which is intended to present a clearer visual presentation for use by the operator.

The operator or other user may virtually position the treatment boundary TB and/or the safety boundary SB on the display screen 14 using an interface other than the control element 30 as described for previous embodiments. For example, the treatment and/or safety boundaries TB and SB may be positioned on a display screen having a real time image of the uterine anatomy using a keyboard, a mouse, a roller ball, a touch screen, voice activation, or any other conventional interface used with computer and other displays. The virtual treatment and/or safety boundaries may be set relative to the actual position of the needle shaft 34 which can be tracked by the system using the image of the shaft in tissue. After the operator is satisfied with the placement of the virtual treatment and/or safety boundaries TB and SB, the operator can then manually advance the needle 56 while the system controller 12 may monitor the advancement through the sensors 37 and 41 in the needle component housing 27. Through visual, audible, or other means, the system can alert the operator when the needle 56 has been advanced by the appropriate distance. After locking the needle, the user can then advance the tines 57 manually while the controller 12 may monitor their position via the sensors 37 and 41. The system may again alert the operator when the tines 57 have been deployed by the appropriate amount within the limits of the virtual treatment and/or safety boundaries TB and SB. The system 12 can then alert the operator that treatment may commence.

FIG. 13 shows a method 1300 for treating a tissue according to embodiments of the present disclosure. The systems and devices described herein may be used to implement the method 1300, including any combination of the steps and sub-steps thereof.

In a step 1301, a real-time display, for example, the display 14 described above, may be provided.

In a step 1306, a treatment region TR may be displayed as described herein.

In a step 1311, a safety region SR may be displayed as described herein.

In a step 1316, the treatment region TR and the safety region SR may be overlapped with the target tissue. For instance, this overlap may be achieved by advancing the treatment probe 16 toward the uterine wall UW and target fibroid F as shown in FIG. 6A.

In a step 1321, target fiducials for the needle and the tines may be displayed, such as on display 14. These target fiducials may be positioned within one or more of the treatment region TR or safety region SR such as described above with respect to FIGS. 10A, 11A, and 12A-12D.

In a step 1331, the needle may be advanced to match its respective target fiducial such as described above with respect to FIG. 10A. Once matched, the user may operate the control element 30 or other user interface to lock the needle position indicating fiducial with the needle target fiducial such that further advancement or retraction of the needle advances or retracts, respectively, the target fiducial as well, as shown on the display. In this manner, the therapeutic target area may be matched to the position of the needle and adjusted accordingly, typically in real-time. Once the needle position indicating fiducial is locked with the needle target fiducial, the size and/or position of the treatment region TR and/or safety region SR may be adjusted in real-time as well.

In a step 1336, the tines may be advanced to match its respective target fiducials such as described above with respect to FIG. 11A. Once the needle position indicating fiducial is locked with the needle target fiducial, the size and/or position of the treatment region TR and/or safety region SR may still be adjusted as well.

In a step 1341, the position of the treatment region TR may be adjusted, such as by manipulating or operating the control element 30 or other user interface as described herein.

In a step 1346, the position of the safety region SR may be adjusted, such as by manipulating or operating the control element 30 or other user interface as described herein.

In a step 1351, the size of the treatment region TR may be adjusted, such as by manipulating or operating the control element 30 or other user interface as described herein.

In a step 1356, the size of the safety region SR may be adjusted, such as by manipulating or operating the control element 30 or other user interface as described herein.

In a step 1361, the target tissue is ablated such as with the treatment probe 16 and when the treatment region TR and safety region SR are sized and positioned as desired and the needle and tines are positioned to their desired positions.

Although the above steps show method 1300 of treating tissue in a patient according to many embodiments, a person of ordinary skill in the art will recognize many variations based on the teaching described herein. The steps may be completed in a different order. Steps may be added or deleted. Some of the steps may comprise sub-steps. Many of the steps may be repeated as often as beneficial to the treatment.

Figure 14:
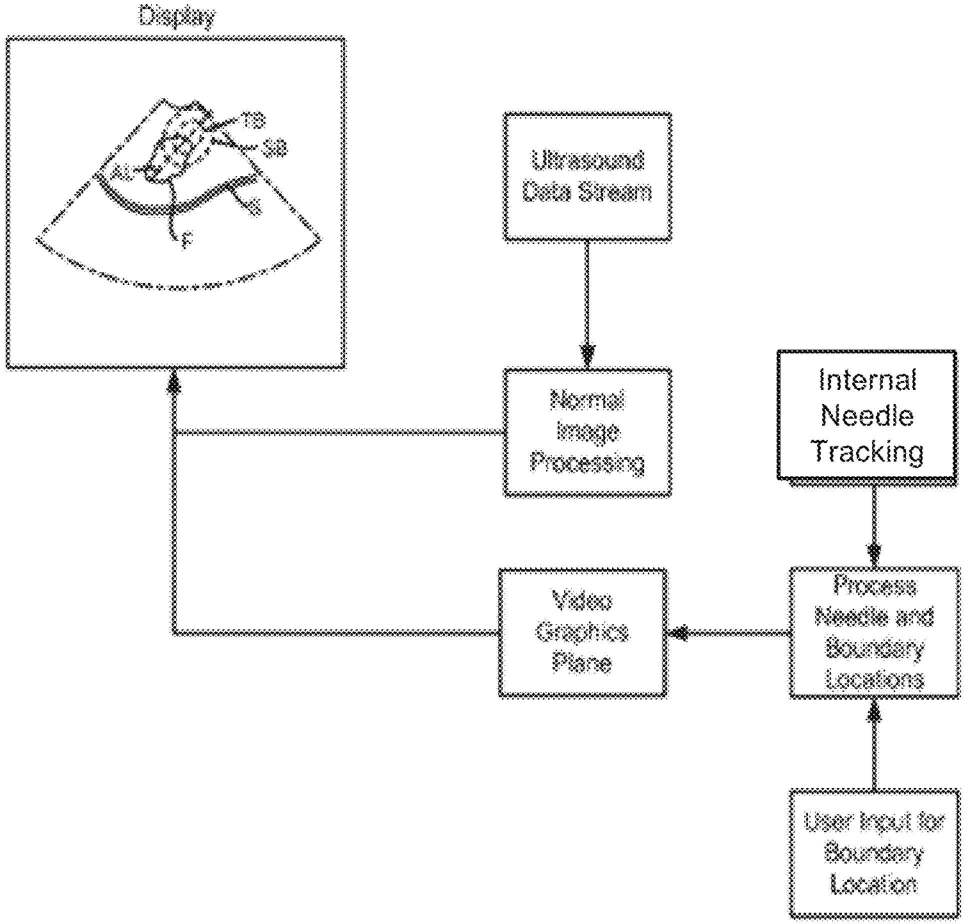
FIG. 14 illustrates a system diagram where needle tracking data is used for tracking the needle position, in accordance with the principles of the present disclosure.

Referring now to FIG. 14, the systems and methods of the present disclosure can rely on internal needle tracking, such as the use of position sensors within the handle component of the needle component of the treatment probe. The position sensors may track and/or determine real-time positions of the needle and the tines in tissue. The real-time data can then be relied on by the system controller to determine whether the needles remain within the boundaries so that both safe and effective treatment can be effected.

Figure 15:
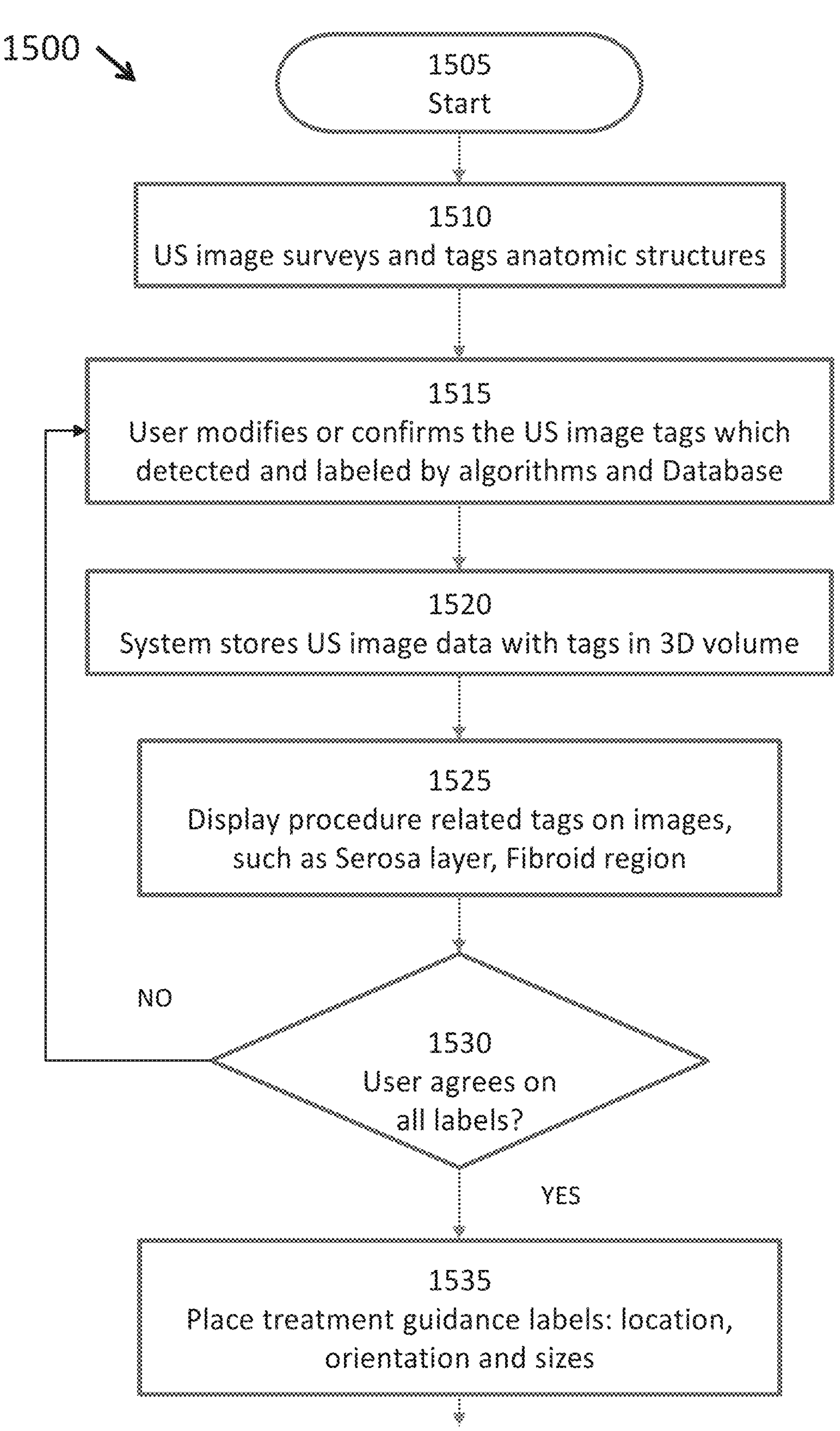
FIG. 15 illustrates a flow chart of an image guided method of treating tissue and image recognition for the treatment method, in accordance with the principles of the present disclosure.
Figure 15:
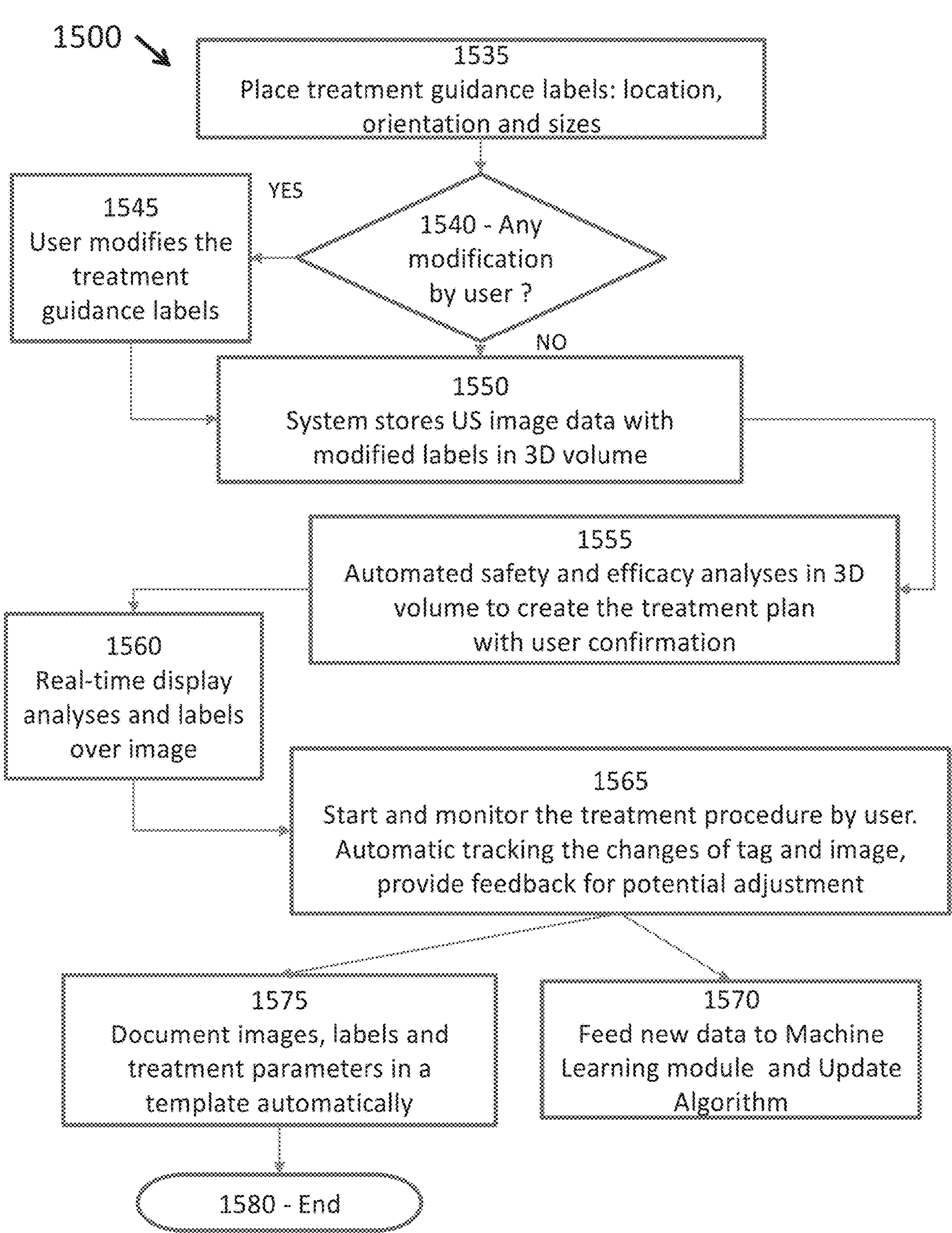

Referring now to FIG. 15, a method 1500 of image guided surgery and iteratively improving image guidance is described. In a step 1505, the method 1500 may be initiated, such as with the operator toggling a control on the system 10. In a step 1510, the system 10 may capture an ultrasound image, such as an intra-uterine ultrasound image as described herein, and, with the aid of the classifier model, label, mark, or tag anatomic structures and/or boundaries. In a step 1515, the operator or user can modify or confirm the ultrasound image tags, marks, or labels, which had been detected and marked or labeled by the classifier model. In a step 1520, the system 10 may store the ultrasound image with the confirmed image tags or labels in a three-dimensional (3D) volume. In a step 1525, procedure related tags may be displayed on the image(s), such as anatomical boundaries showing the serosa, serosal wall, serosa layer, and/or fibroid region. In a step 1530, the operator or user may confirm all the labels. If the operator or user does not agree, the operator or user may edit the tags, boundaries, etc., such as by repeating step 1515 and so forth. In a step 1535, if the user agrees on all the labels, treatment guidance labels, such as for locations, orientations, and sizes of various anatomical features and treatment device elements may be placed on the image, for example, as shown in FIG. 19. In a step 1540, the system 10 may prompt the operator or user for any modifications for the treatment guides. In a step 1545, the operator or user may modify the treatment guidance labels. In a step 1550, if there are no further modifications for the treatment guidance labels, the system may store the ultrasound image data with the modified labels in a three-dimensional (3D) volume. In a step 1555, the system 10 may provide automated three-dimensional (3D) safety and efficacy analyses with user confirmation. These analyses may be performed on a three-dimensional (3D) volume. In a step 1560, the analyses and labels may be placed over the image in real-time. In a step 1565, the operator or user may start and monitor the treatment procedure with the aid of the system 10. The treatment procedure will typically be the uterine fibroid ablation protocol as described herein. In some cases, the anatomy may change through the course of a treatment procedure (for instances, the uterine fibroids may shift in relative location and the treatment probe or its particular elements are moved and/or as other uterine fibroids have been ablated), and to account for that, the system 10 may continually analyze the real-time image to identify anatomical structures and boundaries, updating the displayed tags, labels, and marks along the way. Changes to tag(s) and/or image(s) may be automatically tracked, and feedback may be provided to the operator or user for potential adjustments. In some embodiments, the system 10 may visually and/or audibly alert the user and/or operator for any updates in tags, labels, and marks. In some embodiments, at least some of the steps of method 1500, such as steps 1510, 1515, 1520, 1525, 1530, 1535, 1540, 1545, 1550, 1555, and/or 1560 may be repeated with these updates. In a further step 1570, the system 10 may record the tagged, marked, and/or labeled image as well as the treatment procedure, and the updates and new data may be fed to a machine learning algorithm to train and/or update the machine learning algorithm for classifying image features and/or updating the treatment analyses in real-time during the procedure. In a step 1575, the system 10 may automatically document images, labels, and treatment parameters in a template. In a step 1580, the method 1500 may be ended such as when the treatment procedure has been completed.

Although the above steps show method 1500 of image guided surgery according to many embodiments, a person of ordinary skill in the art will recognize many variations based on the teaching described herein. The steps may be completed in a different order. Steps may be added or deleted. Some of the steps may comprise sub-steps. Many of the steps may be repeated as often as beneficial to the method. At least a portion of the method 1500 may be combined with portions of the method 1300 and/or the method 1600 described above.

In some embodiments, imaging components, systems, and methods described herein include a digital processing device, or use of the same. In further embodiments, the digital processing device includes one or more hardware central processing units (CPUs), general purpose graphics processing units (GPGPUs), or field programmable gate arrays (FPGAs) that carry out the device's functions. In still further embodiments, the digital processing device further comprises an operating system configured to perform executable instructions. In some embodiments, the digital processing device may be optionally connected a computer network. In further embodiments, the digital processing device is optionally connected to the internet such that it accesses the World Wide Web. In still further embodiments, the digital processing device is optionally connected to a cloud computing infrastructure. In other embodiments, the digital processing device is optionally connected to an intranet. In other embodiments, the digital processing device is optionally connected to a data storage device.

In accordance with the description herein, suitable digital processing devices include, by way of non-limiting examples, server computers, desktop computers, laptop computers, notebook computers, sub-notebook computers, netbook computers, netpad computers, set-top computers, media streaming devices, handheld computers, internet appliances, mobile smartphones, tablet computers, personal digital assistants, video game consoles, and vehicles. Those of skill in the art will recognize that many smartphones are suitable for use in the system described herein. Those of skill in the art will also recognize that select televisions, video players, and digital music players with optional computer network connectivity are suitable for use in the system described herein. Suitable tablet computers include those with booklet, slate, and convertible configurations, known to those of skill in the art.

In some embodiments, the digital processing device includes an operating system configured to perform executable instructions. The operating system is, for example, software, including programs and data, which manages the device's hardware and provides services for execution of applications. Those of skill in the art will recognize that suitable server operating systems include, by way of non-limiting examples, FreeBSD, OpenBSD, NetBSD®, Linux, Apple® Mac OS X Server®, Oracle® Solaris®, Windows Server®, and Novell® NetWare®. Those of skill in the art will recognize that suitable personal computer operating systems include, by way of non-limiting examples, Microsoft® Windows®, Apple® Mac OS X®, UNIX®, and UNIX-like operating systems such as GNU/Linux®. In some embodiments, the operating system is provided by cloud computing. Those of skill in the art will also recognize that suitable mobile smart phone operating systems include, by way of non-limiting examples, Nokia® Symbian® OS, Apple® iOS®, Research In Motion® BlackBerry OS®, Google® Android®, Microsoft® Windows Phone® OS, Microsoft® Windows Mobile® OS, Linux®, and Palm® WebOS®. Those of skill in the art will also recognize that suitable media streaming device operating systems include, by way of non-limiting examples, Apple TV®, Roku®, Boxee®, Google TV®, Google Chromecast®, Amazon Fire®, and Samsung® HomeSync®. Those of skill in the art will also recognize that suitable video game console operating systems include, by way of non-limiting examples, Sony® PS3®, Sony® PS4®, Microsoft® Xbox 360®, Microsoft Xbox One, Nintendo® Wii®, Nintendo® Wii U®, and Ouya®.

In some embodiments, the device includes a storage and/or memory device. The storage and/or memory device is one or more physical apparatuses used to store data or programs on a temporary or permanent basis. In some embodiments, the device is volatile memory and requires power to maintain stored information. In some embodiments, the device is non-volatile memory and retains stored information when the digital processing device is not powered. In further embodiments, the non-volatile memory comprises flash memory. In some embodiments, the non-volatile memory comprises dynamic random-access memory (DRAM). In some embodiments, the non-volatile memory comprises ferroelectric random access memory (FRAM). In some embodiments, the non-volatile memory comprises phase-change random access memory (PRAM). In other embodiments, the device is a storage device including, by way of non-limiting examples, CD-ROMs, DVDs, flash memory devices, magnetic disk drives, magnetic tapes drives, optical disk drives, and cloud computing-based storage. In further embodiments, the storage and/or memory device is a combination of devices such as those disclosed herein.

In some embodiments, the digital processing device includes a display to send visual information to a user. In some embodiments, the display is a cathode ray tube (CRT). In some embodiments, the display is a liquid crystal display (LCD). In further embodiments, the display is a thin film transistor liquid crystal display (TFT-LCD). In some embodiments, the display is an organic light emitting diode (OLED) display. In various further embodiments, on OLED display is a passive-matrix OLED (PMOLED) or active-matrix OLED (AMOLED) display. In some embodiments, the display is a plasma display. In other embodiments, the display is a video projector. In still further embodiments, the display is a combination of devices such as those disclosed herein.

In some embodiments, the digital processing device includes an input device to receive information from a user. In some embodiments, the input device is a keyboard. In some embodiments, the input device is a pointing device including, by way of non-limiting examples, a mouse, trackball, track pad, joystick, game controller, or stylus. In some embodiments, the input device is a touch screen or a multi-touch screen. In other embodiments, the input device is a microphone to capture voice or other sound input. In other embodiments, the input device is a video camera or other sensor to capture motion or visual input. In further embodiments, the input device is a Kinect, Leap Motion, or the like. In still further embodiments, the input device is a combination of devices such as those disclosed herein.

Figure 20:
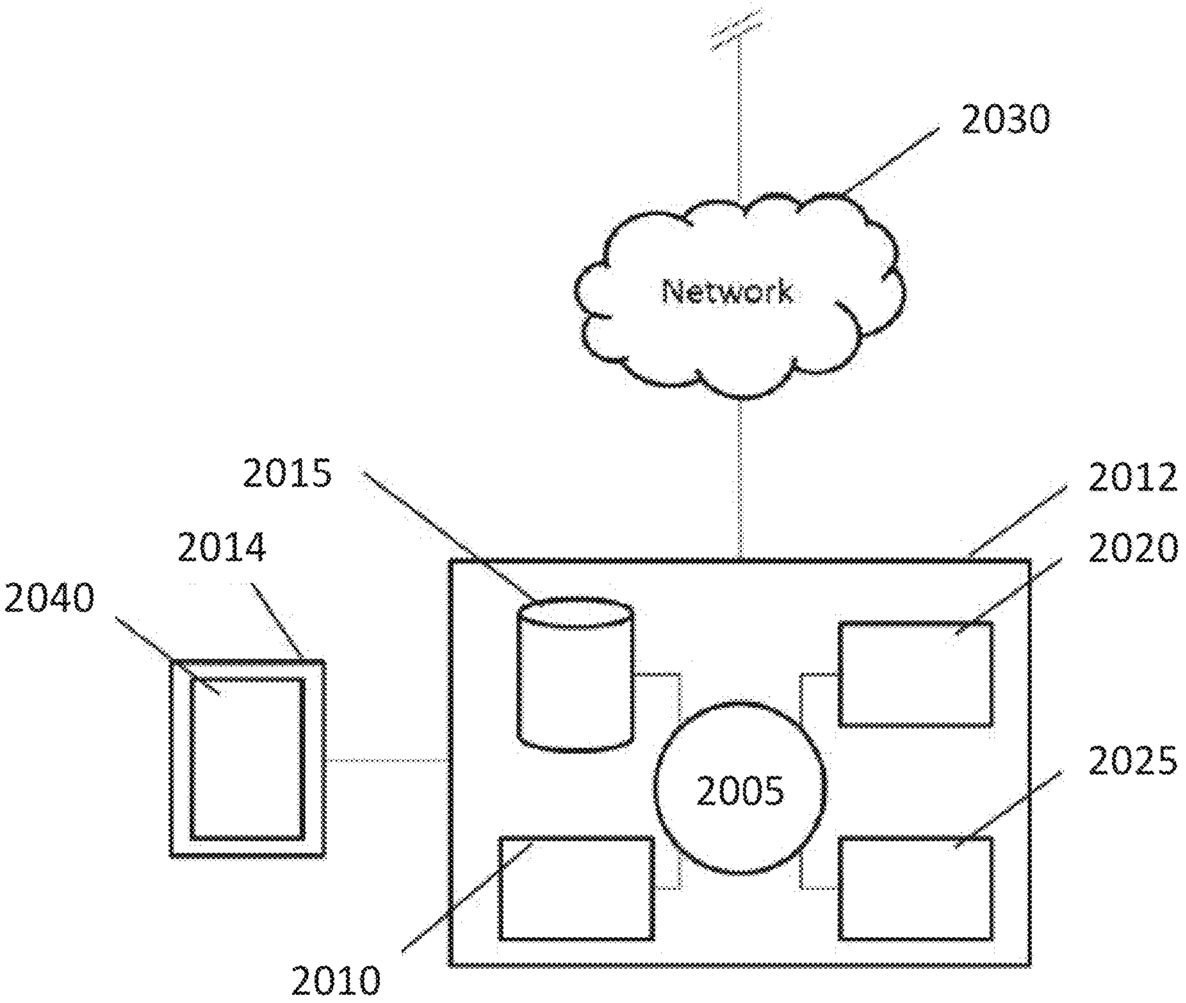
FIG. 20 illustrates a schematic of an exemplary digital processing system programmed or otherwise configured to implement the methods of the present disclosure, in accordance with the principles of the present disclosure.

Referring to FIG. 20, in a particular embodiment, an exemplary digital processing device 2012 is programmed or otherwise configured control to an imaging component and/or instruments as described herein. The device 2012 may regulate various aspects of the imaging component and/or instruments of the present disclosure, such as, for example, performing processing steps. In this embodiment, the digital processing device 2012 includes a central processing unit (CPU, also "processor" and "computer processor" herein) 2005, which may be a single core or multi core processor, or a plurality of processors for parallel processing. The digital processing device 2012 also includes memory or memory location 2010 (e.g., random-access memory, read-only memory, flash memory), electronic storage unit 2015 (e.g., hard disk), communication interface 2020 (e.g., network adapter) for communicating with one or more other systems, and peripheral devices 2025, such as cache, other memory, data storage and/or electronic display adapters. The memory 2010, storage unit 2015, interface 2020 and peripheral devices 2025 are in communication with the CPU 2005 through a communication bus (solid lines), such as a motherboard. The storage unit 2015 may be a data storage unit (or data repository) for storing data. The digital processing device 2012 can be operatively coupled to a computer network ("network") 2030 with the aid of the communication interface 2020. The network 2030 can be the Internet, an internet and/or extranet, or an intranet and/or extranet that is in communication with the Internet. The network 2030 in some cases is a telecommunication and/or data network. The network 2030 can include one or more computer servers, which can enable distributed computing, such as cloud computing. The network 2030, in some cases with the aid of the device 2012, can implement a peer-to-peer network, which may enable devices coupled to the device 2012 to behave as a client or a server.

Continuing to refer to FIG. 20, the CPU 2005 can execute a sequence of machine-readable instructions, which can be embodied in a program or software. The instructions may be stored in a memory location, such as the memory 2010. The instructions can be directed to the CPU 2005, which can subsequently program or otherwise configure the CPU 2005 to implement methods of the present disclosure. Examples of operations performed by the CPU 2005 can include fetch, decode, execute, and write back. The CPU 2005 can be part of a circuit, such as an integrated circuit. One or more other components of the device 2012 can be included in the circuit. In some cases, the circuit is an application specific integrated circuit (ASIC) or a field programmable gate array (FPGA).

Continuing to refer to FIG. 20, the storage unit 2015 can store files, such as drivers, libraries and saved programs. The storage unit 2015 can store user data, e.g., user preferences and user programs. The digital processing device 2012 in some cases can include one or more additional data storage units that are external, such as located on a remote server that is in communication through an intranet or the Internet. The digital processing device 2012 can communicate with one or more remote computer systems through the network 2030. For instance, the device 2012 can communicate with a remote computer system of a user.

Examples of remote computer systems include personal computers (e.g., portable PC), slate or tablet PCs (e.g., Apple® iPad, Samsung® Galaxy Tab), telephones, Smart phones (e.g., Apple® iPhone, Android-enabled device, Blackberry®), or personal digital assistants.

Methods as described herein can be implemented by way of machine (e.g., computer processor) executable code stored on an electronic storage location of the digital processing device 2012, such as, for example, on the memory 2010 or electronic storage unit 2015. The machine executable or machine-readable code can be provided in the form of software. During use, the code can be executed by the processor 2005. In some cases, the code can be retrieved from the storage unit 2015 and stored on the memory 2010 for ready access by the processor 1005. In some situations, the electronic storage unit 2015 can be precluded, and machine-executable instructions are stored on memory 2010.

The digital processing device 2012 can include or be in communication with an electronic display 2014 that comprises a user interface (UI) 20040. Examples of UI's include, without limitation, a graphical user interface (GUI) and web-based user interface. In some cases, electronic display 2014 may be connected to the computer system 2012 via a network, e.g., via network 2030.

In some embodiments, the platforms, systems, media, and methods disclosed herein include one or more non-transitory computer readable storage media encoded with a program including instructions executable by the operating system of an optionally networked digital processing device. In further embodiments, a computer readable storage medium is a tangible component of a digital processing device. In still further embodiments, a computer readable storage medium is optionally removable from a digital processing device. In some embodiments, a computer readable storage medium includes, by way of non-limiting examples, CD-ROMs, DVDs, flash memory devices, solid state memory, magnetic disk drives, magnetic tape drives, optical disk drives, cloud computing systems and services, and the like. In some cases, the program and instructions are permanently, substantially permanently, semi-permanently, or non-transitorily encoded on the media.

In some embodiments, the platforms, systems, media, and methods disclosed herein include at least one computer program, or use of the same. A computer program includes a sequence of instructions, executable in the digital processing device's CPU, written to perform a specified task. Computer readable instructions may be implemented as program modules, such as functions, objects, Application Programming Interfaces (APIs), data structures, and the like, that perform particular tasks or implement particular abstract data types. In light of the disclosure provided herein, those of skill in the art will recognize that a computer program may be written in various versions of various languages.

The functionality of the computer readable instructions may be combined or distributed as desired in various environments. In some embodiments, a computer program comprises one sequence of instructions. In some embodiments, a computer program comprises a plurality of sequences of instructions. In some embodiments, a computer program is provided from one location. In other embodiments, a computer program is provided from a plurality of locations. In various embodiments, a computer program includes one or more software modules. In various embodiments, a computer program includes, in part or in whole, one or more web applications, one or more mobile applications, one or more standalone applications, one or more web browser plug-ins, extensions, add-ins, or add-ons, or combinations thereof.

In some embodiments, a computer program includes a web application. In light of the disclosure provided herein, those of skill in the art will recognize that a web application, in various embodiments, utilizes one or more software frameworks and one or more database systems. In some embodiments, a web application is created upon a software framework such as Microsoft® .NET or Ruby on Rails (RoR). In some embodiments, a web application utilizes one or more database systems including, by way of non-limiting examples, relational, non-relational, object oriented, associative, and XML database systems. In further embodiments, suitable relational database systems include, by way of non-limiting examples, Microsoft® SQL Server, mySQL™, and Oracle®. Those of skill in the art will also recognize that a web application, in various embodiments, is written in one or more versions of one or more languages. A web application may be written in one or more markup languages, presentation definition languages, client-side scripting languages, server-side coding languages, database query languages, or combinations thereof. In some embodiments, a web application is written to some extent in a markup language such as Hypertext Markup Language (HTML), Extensible Hypertext Markup Language (XHTML), or eXtensible Markup Language (XML). In some embodiments, a web application is written to some extent in a presentation definition language such as Cascading Style Sheets (CSS). In some embodiments, a web application is written to some extent in a client-side scripting language such as Asynchronous Javascript and XML (AJAX), Flash® ActionScript, JavaScript, or Silverlight®. In some embodiments, a web application is written to some extent in a server-side coding language such as Active Server Pages (ASP), ColdFusion®, Perl, Java™, JavaServer Pages (JSP), Hypertext Preprocessor (PHP), Python™, Ruby, Tcl, Smalltalk, WebDNA®, or Groovy. In some embodiments, a web application is written to some extent in a database query language such as Structured Query Language (SQL). In some embodiments, a web application integrates enterprise server products such as IBM® Lotus Domino®. In some embodiments, a web application includes a media player element. In various further embodiments, a media player element utilizes one or more of many suitable multimedia technologies including, by way of non-limiting examples, Adobe® Flash®, HTML 5, Apple® QuickTime®, Microsoft® Silverlight®, Java™, and Unity®.

In some embodiments, a computer program includes a mobile application provided to a mobile digital processing device. In some embodiments, the mobile application is provided to a mobile digital processing device at the time it is manufactured. In other embodiments, the mobile application is provided to a mobile digital processing device via the computer network described herein.

In view of the disclosure provided herein, a mobile application is created by techniques known to those of skill in the art using hardware, languages, and development environments known to the art. Those of skill in the art will recognize that mobile applications are written in several languages. Suitable programming languages include, by way of non-limiting examples, C, C++, C#, Objective-C, Java™, JavaScript, Pascal, Object Pascal, Python™, Ruby, VB.NET, WML, and XHTML/HTML with or without CSS, or combinations thereof.

Suitable mobile application development environments are available from several sources. Commercially available development environments include, by way of non-limiting examples, AirplaySDK, alcheMo, Appcelerator®, Celsius, Bedrock, Flash Lite, .NET Compact Framework, Rhomobile, and WorkLight Mobile Platform. Other development environments are available without cost including, by way of non-limiting examples, Lazarus, MobiFlex, MoSync, and PhoneGap. Also, mobile device manufacturers distribute software developer kits including, by way of non-limiting examples, iPhone and iPad (iOS) SDK, Android™ SDK, BlackBerry® SDK, BREW SDK, Palm® OS SDK, Symbian SDK, webOS SDK, and Windows® Mobile SDK.

Those of skill in the art will recognize that several commercial forums are available for distribution of mobile applications including, by way of non-limiting examples, Apple® App Store, Google® Play, Chrome WebStore, BlackBerry® App World, App Store for Palm devices, App Catalog for webOS, Windows® Marketplace for Mobile, Ovi Store for Nokia® devices, Samsung® Apps, and Nintendo® DSi Shop.

In some embodiments, a computer program includes a standalone application, which is a program that is run as an independent computer process, not an add-on to an existing process, e.g., not a plug-in. Those of skill in the art will recognize that standalone applications are often compiled. A compiler is a computer program(s) that transforms source code written in a programming language into binary object code such as assembly language or machine code. Suitable compiled programming languages include, by way of non-limiting examples, C, C++, Objective-C, COBOL, Delphi, Eiffel, Java™, Lisp, Python™, Visual Basic, and VB .NET, or combinations thereof. Compilation is often performed, at least in part, to create an executable program. In some embodiments, a computer program includes one or more executable complied applications.

In some embodiments, the computer program includes a web browser plug-in (e.g., extension, etc.). In computing, a plug-in is one or more software components that add specific functionality to a larger software application. Makers of software applications support plug-ins to enable third-party developers to create abilities which extend an application, to support easily adding new features, and to reduce the size of an application. When supported, plug-ins enable customizing the functionality of a software application. For example, plug-ins are commonly used in web browsers to play video, generate interactivity, scan for viruses, and display particular file types. Those of skill in the art will be familiar with several web browser plug-ins including, Adobe® Flash® Player, Microsoft® Silverlight®, and Apple® QuickTime®. In some embodiments, the toolbar comprises one or more web browser extensions, add-ins, or add-ons. In some embodiments, the toolbar comprises one or more explorer bars, tool bands, or desk bands.

In view of the disclosure provided herein, those of skill in the art will recognize that several plug-in frameworks are available that enable development of plug-ins in various programming languages, including, by way of non-limiting examples, C++, Delphi, Java™ PHP, Python™, and VB .NET, or combinations thereof.

Web browsers (also called Internet browsers) are software applications, designed for use with network-connected digital processing devices, for retrieving, presenting, and traversing information resources on the World Wide Web. Suitable web browsers include, by way of non-limiting examples, Microsoft® Internet Explorer®, Mozilla® Firefox®, Google® Chrome, Apple® Safari®, Opera Software® Opera®, and KDE Konqueror. In some embodiments, the web browser is a mobile web browser. Mobile web browsers (also called mircrobrowsers, mini-browsers, and wireless browsers) are designed for use on mobile digital processing devices including, by way of non-limiting examples, handheld computers, tablet computers, netbook computers, subnotebook computers, smartphones, music players, personal digital assistants (PDAs), and handheld video game systems. Suitable mobile web browsers include, by way of non-limiting examples, Google® Android® browser, RIM BlackBerry® Browser, Apple® Safari®, Palm® Blazer, Palm® WebOS® Browser, Mozilla® Firefox® for mobile, Microsoft® Internet Explorer® Mobile, Amazon® Kindle® Basic Web, Nokia® Browser, Opera Software® Opera® Mobile, and Sony® PSP™ browser.

Software Modules

In some embodiments, the platforms, systems, media, and methods disclosed herein include software, server, and/or database modules, or use of the same. In view of the disclosure provided herein, software modules are created by techniques known to those of skill in the art using machines, software, and languages known to the art. The software modules disclosed herein are implemented in a multitude of ways. In various embodiments, a software module comprises a file, a section of code, a programming object, a programming structure, or combinations thereof. In further various embodiments, a software module comprises a plurality of files, a plurality of sections of code, a plurality of programming objects, a plurality of programming structures, or combinations thereof. In various embodiments, the one or more software modules comprise, by way of non-limiting examples, a web application, a mobile application, and a standalone application. In some embodiments, software modules are in one computer program or application. In other embodiments, software modules are in more than one computer program or application. In some embodiments, software modules are hosted on one machine. In other embodiments, software modules are hosted on more than one machine. In further embodiments, software modules are hosted on cloud computing platforms. In some embodiments, software modules are hosted on one or more machines in one location. In other embodiments, software modules are hosted on one or more machines in more than one location.

In some embodiments, the platforms, systems, media, and methods disclosed herein include one or more databases, or use of the same. In view of the disclosure provided herein, those of skill in the art will recognize that many databases are suitable for storage and retrieval of information. In various embodiments, suitable databases include, by way of non-limiting examples, relational databases, non-relational databases, object-oriented databases, object databases, entity-relationship model databases, associative databases, and XML databases. Further non-limiting examples include SQL, PostgreSQL, MySQL, Oracle, DB2, and Sybase. In some embodiments, a database is internet-based. In further embodiments, a database is web-based. In still further embodiments, a database is cloud computing-based. In other embodiments, a database is based on one or more local computer storage devices.

While preferred embodiments of the present disclosure have been shown and described herein, it will be obvious to those skilled in the art that such embodiments are provided by way of example only. Numerous variations, changes, and substitutions will now occur to those skilled in the art without departing from the present disclosure. It should be understood that various alternatives to the embodiments of the present disclosure described herein may be employed in practicing the invention. It is intended that the following claims define the scope of the invention and that methods and structures within the scope of these claims and their equivalents be covered thereby.

What is claimed is:

1. A computer-implemented method of planning and implementing a treatment procedure, the method comprising:

(i) displaying a real-time operating field image to a user;

(ii) identifying one or more of (a) at least one anatomical feature or (b) at least one anatomical boundary on the real-time operating field image, with the aid of the trained classifier model;

(iii) displaying one or more of (a) at least one label for the identified at least one anatomical feature or (b) at least one marking for the identified at least one anatomical boundary on the displayed real-time operating field image;

(iv) allowing the user to modify the real-time operating field image by one or more of (a) re-labelling the identified at least one anatomical feature or (b) re-positioning the at least one marking for the at least one anatomical boundary; and (v) providing an update to the trained classifier model based on the modifications by the user;

wherein the trained classifier model is generated by:

(vi) displaying an operating field image to a user;

(vii) establishing the at least one anatomical boundary in the operating field image, the at least one anatomical boundary being marked by the user;

(viii) labelling the at least one anatomical feature separated by the at least one anatomical boundary in the operating field image, the at least one anatomical feature being labeled by user without the aid of the classifier model; and (ix) repeating steps (vi) to (viii) to generate a training set of operating field images each with the at least one marked anatomical boundary and the at least one labeled anatomical feature; and (x) training the classifier model, based on the training set of operating field images, to identify (a) the at least one anatomical feature or (b) the at least one anatomical boundary on the realtime operating image.

2. The method of claim 1, wherein the trained classifier model is updated at step (v) by adding the modified real-time operating field image from step (iv) to the training set of operating field images and updating the classifier model based on the set of operating field images with the added modified real-time operating field image.

3. A computer-implemented method of planning and implementing a treatment procedure, the method comprising:

(i) displaying a real-time operating field image to a user;

(ii) identifying one or more of (a) at least one anatomical feature or (b) at least one anatomical boundary on the real-time operating field image, with the aid of the trained classifier model;

(iii) displaying one or more of (a) at least one label for the identified at least one anatomical feature or (b) at least one marking for the identified at least one anatomical boundary on the displayed real-time operating field image;

(iv) allowing the user to modify the real-time operating field image by one or more of (a) re-labelling the identified at least one anatomical feature or (b) re-positioning the at least one marking for the at least one anatomical boundary;

(v) confirming with the user the modification to the real-time operating field image; and (vi) providing an update to the trained classifier model in response to the confirmation of the modification to the real-time operating field image by the user.

4. The method of claim 3, wherein providing the update to the trained classifier model comprises adding the modified real-time operating field image to a training set of operating field images.

5. The method of claim 1, wherein the operating field image at step (i) is a surgical field image.

6. The method of claim 1, further comprising treating an anatomical structure based on one or more of (a) the displayed at least one label for the at least one identified anatomical feature or (b) the displayed at least one marking for the at least one anatomical boundary on the real-time operating field image.

7. The method of claim 6, wherein the treated anatomical structure is a uterine fibroid.

8. The method of claim 6, further comprising repeating steps (ii) to (iv) in real-time during the treatment procedure.

9. The method of claim 6, further comprising repeating one or more of steps (ii) or (iii) after the treatment procedure to identify one or more changes to the anatomical structure from the treatment procedure.

10. The method of claim 1, wherein the operating field image at step (i) comprises an ultrasound image.

11. The method of claim 10, wherein the ultrasound image is an intra-uterine ultrasound image.

12. The method of claim 1, wherein the operating field image at step (i) comprises an image of a uterus of a patient.

13. The method of claim 12, wherein at least one marking for the at least one anatomical boundary separates a plurality of anatomical features of the uterus, the plurality of anatomical features including one or more of a serosa, a myometrium, a fibroid, a uterine wall, a bladder wall, or a bladder.

14. The method of claim 12, wherein the at least one label for the at least one anatomical feature includes one or more of a serosa, a myometrium, a fibroid, a uterine wall, a bladder wall, or a bladder.

15. The method of claim 1, wherein the trained classifier model comprises a machine learning algorithm.

16. The method of claim 15, wherein the machine learning algorithm is a convolutional deep learning network.

17. The method of claim 1, wherein the trained classifier model is one or more of a binary tree, a random forest, a decision tree, a plurality of decision trees, a plurality of decision trees with controlled variance, a multinomial logistic regression, a naive Bayes classifier, a linear classifier, an ensemble of linear classifiers, a boosting algorithm, a boosting algorithm trained with stochastic gradient descent, a boosting algorithm trained with stochastic gradient descent, a boosting algorithm comprising training data weighting, a boosting algorithm comprising updating training data weighting, or a boosting algorithm comprising updating misclassified training data with higher weights.

18. The method of claim 1, further comprising providing a pre-treatment image to the user as a guide for identifying the one or more of (a) the at least one anatomical feature or (b) the at least one anatomical boundary on the real-time operating field image.

19. The method of claim 18, wherein the pre-treatment image comprises one or more of an MM image, an X-ray image, a CT image, or an ultrasound image.

20. A computer-implemented method of planning and implementing a treatment procedure, the method comprising:

(i) displaying a real-time operating field image to a user;

(ii) identifying one or more of (a) at least one anatomical feature or (b) at least one anatomical boundary on the real-time operating field image, with the aid of the trained classifier model, and without the aid of any label used to identify the at least one anatomical feature and without the aid of any manually made marking by the user for the at least one anatomical boundary;

(iii) displaying one or more of (a) at least one label for the identified at least one anatomical feature or (b) at least one marking for the identified at least one anatomical boundary on the displayed real-time operating field image;

(iv) allowing the user to modify the real-time operating field image by one or more of (a) re-labelling the identified at least one anatomical feature or (b) re-positioning the at least one marking for the at least one anatomical boundary; and (v) providing an update to the trained classifier model based on the modifications by the user.

21. The method of claim 20, further comprising prompting the user to confirm that the at least one label for the identified at least one anatomical feature or (b) the at least one marking for the identified at least one anatomical boundary on the displayed real-time operating field image is correct, wherein step (iv) is performed if the user does not confirm that the at least one label for the identified at least one anatomical feature or (b) the at least one marking for the identified at least one anatomical boundary on the displayed real-time operating field image is correct.

22. The method of claim 3, further comprising treating an anatomical structure based on one or more of (a) the displayed at least one label for the at least one identified anatomical feature or (b) the displayed at least one marking for the at least one anatomical boundary on the real-time operating field image.

* * * * *